United States Patent

Ishihara et al.

[11] Patent Number: 5,298,516
[45] Date of Patent: Mar. 29, 1994

[54] THIA ZOLIDONE COMPOUNDS AND METHOD OF USING THE SAME AS A VASODILATOR

[75] Inventors: Sadao Ishihara; Fujio Saito; Takao Yoshioka; Hiroyuki Koike; Shigeki Miyake; Hiroshi Mizuno, all of Tokyo, Japan

[73] Assignee: Sankyo Company, Limited, Tokyo, Japan

[21] Appl. No.: 856,491

[22] Filed: Mar. 24, 1992

[30] Foreign Application Priority Data

Mar. 27, 1991 [JP] Japan .................................. 3-63088
May 8, 1991 [JP] Japan .................................. 3-102751
Dec. 13, 1991 [JP] Japan .................................. 3-330304

[51] Int. Cl.$^5$ .................... C07D 77/14; A61K 31/425
[52] U.S. Cl. .................... 514/369; 514/342; 546/280; 548/188
[58] Field of Search .............. 548/188; 546/280; 514/369, 342

[56] References Cited

U.S. PATENT DOCUMENTS 4,200,640  4/1980  Nagano et al. ...................... 548/316
4,923,886  5/1990  Shiokawa ........................... 514/365

Primary Examiner—Robert Gerstl
Attorney, Agent, or Firm—Frishauf, Holtz, Goodman & Woodward

[57] ABSTRACT

Compounds of formula (I):

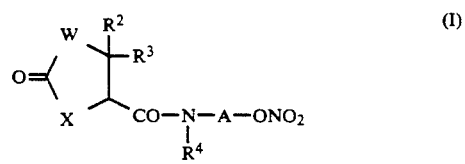

wherein W represents a sulfur atom and X represents a group of formula $-N(R^1)-$, or W represents a group of formula $-N(R^1)-$ and X represents a sulfur atom; $R^1$ is hydrogen, alkyl or aralkyl; $R^2$ and $R^3$ are each hydrogen, alkyl, aralkyl, aryl or aromatic heterocyclic; $R^4$ is hydrogen, alkyl or aralkyl; and A is alkylene which is optionally substituted by carboxy; and pharmaceutically acceptable salts and esters thereof, have a valuable vasodilatory activity.

29 Claims, No Drawings

THIAZOLIDONE COMPOUNDS AND METHOD OF USING THE SAME AS A VASODILATOR

BACKGROUND OF THE INVENTION

The present invention relates to a series of new thiazolidinone and oxazolidinone derivatives containing a nitrooxyalkylcarbamoyl group, and provides methods and compositions using these compounds as vasodilators, e.g. in the therapy and prophylaxis of cardiovascular diseases; the invention also provides processes for their preparation.

Cardiovascular diseases are a well known and increasing cause of death and disability in the world, and considerable efforts have been expended in a search for drugs capable of treating or preventing such diseases.

Nitroglycerin is frequently used, and has been used for many years, for the therapy of cardiovascular diseases, particularly angina pectoris, but this compound has several disadvantages when used as a medicine. For example, the compound is easily inactivated in the liver (the "first-pass effect") and the duration of the effect is very short. Furthermore, the medicine sometimes causes adverse reactions, such as cephalalgia, vertigo and tachycardia, as a result of its reducing the patient's blood pressure. It has, therefore, been desired for many years to discover anti-anginal drugs showing a long lasting effect but which do not have the problem of the first-pass effect.

We have now discovered a series of compounds which we believe achieve this aim.

The closest prior art to the compounds of the present invention is believed to be U.S. Pat. No. 4 200 640, which describes a number of compounds including N-(2-nitrooxyethyl)-3-pyridinecarboxamide, which is said to have activity as a coronary vasodilator.

The compounds of the present invention resemble the prior art compound in having a nitrooxyalkylcarbamoyl group, but differ in that they include a thiazolidinone or oxazolidinone group. These compounds also have vasodilatory activity, and, because they have few adverse effects, they are expected to be of use for the treatment and prophylaxis of cardiovascular disorders or insufficiency, such as angina pectoris.

BRIEF SUMMARY OF THE INVENTION

It is, therefore, an object of the present invention to provide a series of new thiazolidinone and oxazolidinone derivatives containing a nitrooxyalkylcarbamoyl group.

It is a further, and more specific, object of the present invention to provide such compounds having vasodilatory activity.

Other objects and advantages of the present invention will become apparent as the description proceeds.

The compounds of the present invention are those compounds of formula (I):

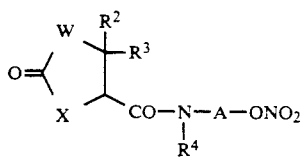

wherein:

W represents a sulfur or oxygen atom and X represents a group of formula —N(R$^1$)—, or W represents a group of formula —N(R$^1$)— and X represents a sulfur or oxygen atom;

R$^1$ represents a hydrogen atom, an alkyl group having from 1 to 6 carbon atoms or an aralkyl group in which an aryl group, as defined below, is a substituent on an alkyl group having from 1 to 4 carbon atoms; R$^2$ and R$^3$ are independently selected from the group consisting of:

hydrogen atoms;

alkyl groups having from 1 to 6 carbon atoms;

aralkyl groups in which an aryl group, as defined below, is a substituent on an alkyl group having from 1 to 4 carbon atoms;

aryl groups, as defined below;

aromatic heterocyclic groups having an aromatic ring containing 5 or 6 ring atoms of which from 1 to 3 are hetero-atoms selected from the group consisting of nitrogen, oxygen and sulfur atoms and the remaining ring atoms are carbon, said heterocyclic group being unsubstituted or being substituted by at least one substituent selected from the group consisting of substituents (a), defined below; and fused ring systems in which an aromatic heterocyclic group, as defined above, is fused to a benzene ring;

R$^4$ represents a hydrogen atom, an alkyl group having from 1 to 6 carbon atoms or an aralkyl group in which an aryl group, as defined below, is a substituent on an alkyl group having from 1 to 4 carbon atoms; and A represents an alkylene group having from 2 to 6 carbon atoms in a straight or branched carbon chain and being unsubstituted or being substituted by at least one carboxy substituent;

said aryl groups have from 6 to 10 ring carbon atoms in at least one aromatic ring and are unsubstituted or are substituted by at least one substituent selected from the group consisting of substituents (b), defined below;

substituents (a) are selected from the group consisting of:

alkyl groups having from 1 to 6 carbon atoms; and groups of formula —NR$^a$R$^b$, where R$^a$ and R$^b$ are independently selected from the group consisting of hydrogen atoms and alkyl groups having from 1 to 6 carbon atoms;

substituents (b) are selected from the group consisting of:

alkyl groups having from 1 to 6 carbon atoms; alkoxy groups having from 1 to 6 carbon atoms; halogen atoms; groups of formula —NR$^a$R$^b$, where R$^a$ and R$^b$ are as defined above; hydroxy groups; and nitro groups;

and pharmaceutically acceptable salts and esters thereof.

The invention also provides a composition for the the treatment and prophylaxis of cardiovascular disorders or insufficiency, said composition comprising an effective amount of at least one coronary vasodilator in admixture with a pharmaceutically acceptable carrier or diluent, wherein said coronary vasodilator is selected from the group consisting of compounds of formula (I) and pharmaceutically acceptable salts and esters thereof.

The invention also provides a method for the treatment or prophylaxis of cardiovascular disorders or insufficiency, which comprises administering at least one coronary vasodilator to a mammal, e.g. a human being, suffering from or susceptible to cardiovascular disorders or insufficiency, wherein said coronary vasodilator is selected from the group consisting of compounds of formula (I) and pharmaceutically acceptable salts and esters thereof.

The invention still further provides processes for the preparation of compounds of formula (I) and pharmaceutically acceptable salts and esters thereof, which are described in more detail hereafter.

DETAILED DESCRIPTION OF INVENTION

The compounds of the present invention are either thiazolidinone or oxazolidinone derivatives, and the nitrooxyalkylcarbamoyl group may be at either the 4-position [W represents an oxygen or sulfur atom and X represents the group of formula $—N(R^1)—$] or the 5-position [W represents the group of formula $—N(R^1)—$ and X represents an oxygen or sulfur atom], which compounds may be represented by the formulae (Ia) and (Ib), respectively:

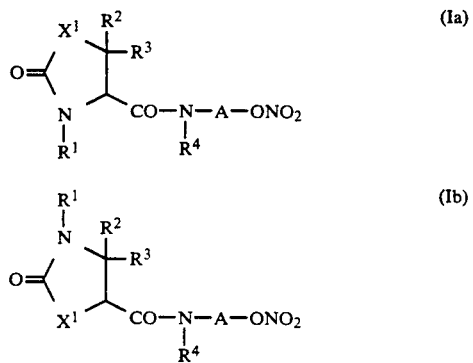

wherein A, $R^1$, $R^2$, $R^3$ and $R^4$ are as defined above, and $X^1$ represents an oxygen or sulfur atom.

In the compounds of the present invention, where $R^1$, $R^2$, $R^3$, $R^4$, $R^a$, $R^b$, substituent (a) or substituent (b) represents an alkyl group having from 1 to 6 carbon atoms, this may be a straight or branched chain group having from 1 to 6 carbon atoms, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups, of which we prefer those alkyl groups having from 1 to 4 carbon atoms. More preferably $R^1$, $R^2$, $R^3$, $R^4$, $R^a$, $R^b$, substituent (a) and substituent (b) are the same or different and each represents an alkyl group having 1 or 2 carbon atoms, most preferably the methyl group.

Where $R^2$ or $R^3$ represents an aryl group, this has from 6 to 10 ring carbon atoms in at least one aromatic ring and is either unsubstituted or is substituted by at least one substituent selected from the group consisting of substituents (b), defined above and exemplified below. The group more preferably has 6 or 10 ring carbon atoms and is still more preferably a phenyl or naphthyl (1- or 2-naphthyl) group, which may be substituted or unsubstituted, of which the phenyl group is most preferred. Where the group is substituted, there is no particular limitation on the number of substituents, except such as may be imposed by the number of substitutable positions or possibly by steric constraints, however, in general, from 1 to 3 substituents are preferred. More preferably the group has 1 substituent or is unsubstituted, and most preferably the group is unsubstituted.

Examples of substituted groups include the 2-, 3- and 4-nitrophenyl, 2-, 3- and 4-chlorophenyl, 2,4-dichlorophenyl, 3,5-dichlorophenyl, 2,4,6-trichlorophenyl, 2-, 3- and 4-fluorophenyl, 2,4-difluorophenyl, 3,5-difluorophenyl, 2,4,6-trifluorophenyl, 2-, 3- and 4-bromophenyl, 2,4-dibromophenyl, 3,5-dibromophenyl, 2,4,6-tribromophenyl, 2-, 3- and 4-methoxyphenyl, 2,4-dimethoxyphenyl, 3,5-dimethoxyphenyl, 2,4,6-trimethoxyphenyl, 2-, 3- and 4-methylphenyl, 2,4-dimethylphenyl, 3,5-dimethylphenyl, 2,4,6-trimethylphenyl, 2-, 3- and 4-hydroxyphenyl, 2,4-dihydroxyphenyl, 3,5-dihydroxyphenyl, 2,4,6-trihydroxyphenyl, 2-, 3- and 4-aminophenyl, 2,4-diaminophenyl, 3,5-diaminophenyl, 2,4,6-triaminophenyl and 2-, 3- and 4-methylaminophenyl groups. Of these, the phenyl, 1-naphthyl, 2-naphthyl, 3-nitrophenyl, 4-chlorophenyl, 2-, 3- or 4-methoxyphenyl, 2-, 3- or 4-methylphenyl, 4-fluorophenyl and 2-, 3- or 4-hydroxyphenyl groups are preferred, and the phenyl, 4-methoxyphenyl, 4-methyl phenyl and 4-hydroxyphenyl groups are most preferred.

Where $R^1$, $R^2$, $R^3$ or $R^4$ represents an aralkyl group, this is an alkyl group having from 1 to 4 carbon atoms which is substituted by at least one aryl group. The alkyl group may be a straight or branched chain group having from 1 to 4, preferably from 1 to 3, carbon atoms; more preferably it has 1 or 2 carbon atoms and most preferably it has 1. Examples of such alkyl groups include those alkyl groups having from 1 to 4 carbon atoms and included in the alkyl groups exemplified above in relation to $R^1$ and other groups. The aryl part of the aralkyl group may be as defined and exemplified above in relation to the aryl groups which may be represented by $R^2$ and $R^3$. The aryl part of the group is either unsubstituted or is substituted by at least one substituent selected from the group consisting of substituents (b), defined above and exemplified below. Where the group is substituted, there is no particular limitation on the number of substituents, except such as may be imposed by the number of substitutable positions or possibly by steric constraints, however, in general, from 1 to 3 substituents are preferred. More preferably the group has 1 substituent or is unsubstituted, and most preferably the group is unsubstituted. Examples of unsubstituted groups include the benzyl, phenethyl, 1-phenylethyl, 1-phenylpropyl, 2-phenylpropyl, 3-phenylpropyl, 4-phenylbutyl, diphenylmethyl (benzhydryl), triphenylmethyl (trityl), 1-naphthylmethyl and 2-naphthylmethyl groups, of which the benzyl and phenethyl groups are preferred. Examples of substituted groups include any of the unsubstituted groups listed above but which is substituted by at least one of substituents (a), especially the 2-, 3- and 4-nitrobenzyl, 2-, 3- and 4-chlorobenzyl, 2,4-dichlorobenzyl, 3,5-dichlorobenzyl, 2,4,6-trichlorobenzyl, 2-, 3- and 4-fluorobenzyl, 2,4-difluorobenzyl, 3,5-difluorobenzyl, 2,4,6-trifluorobenzyl, 2-, 3 and 4-bromobenzyl, 2,4-dibromobenzyl, 3,5-dibromobenzyl, 2,4,6-tribromobenzyl, 2-, 3- and 4-methoxybenzyl, 2,4-dimethoxybenzyl, 3,5-dimethoxybenzyl, 2,4,6-trimethoxybenzyl, 2-, 3- and 4-methylbenzyl, 2,4-dimethylbenzyl, 3,5-dimethylbenzyl, 2,4,6-trimethyl benzyl, 2-, 3- and 4-hydroxybenzyl, 2,4-dihydroxy benzyl, 3,5-dihydroxybenzyl, 2,4,6-trihydroxybenzyl, 2-, 3- and 4-aminobenzyl, 2,4-diaminobenzyl, 3,5-diaminobenzyl, 2,4,6-triaminobenzyl and 2-, 3- and 4-methylaminobenzyl groups. Of these, the benzyl, l-naphthylmethyl, 2-naphthylmethyl, 3-nitrobenzyl, 4-chlorobenzyl, 2-, 3- or 4-methoxybenzyl, 2- , 3- or 4-methylbenzyl, 4-fluorobenzyl and 2-, 3- or 4-hydroxybenzyl groups are preferred, the benzyl, 4-methoxybenzyl, 4-methylbenzyl and 4-hydroxybenzyl groups are more preferred, and the benzyl group is most preferred.

Where $R^2$ or $R^3$ represents a heterocyclic group, this is an aromatic heterocyclic group having an aromatic heterocyclic ring containing 5 or 6 ring atoms of which from 1 to 3 are hetero-atoms selected from the group consisting of nitrogen, oxygen and sulfur atoms and the remaining ring atoms are carbon. The heterocyclic group may be unsubstituted or it may be substituted by at least one substituent selected from the group consisting of substituents (a), defined above and exemplified below, or such a substituted or unsubstituted aromatic heterocyclic group may be fused to a benzene ring. Where there are 3 hetero-atoms, we prefer that at least one (more preferably 2) should be a nitrogen atom and one or two should be nitrogen, oxygen or sulfur atoms (and, where there are two, they may be the same or different). Where there are two hetero-atoms, these may be the same or different and they are selected from nitrogen, oxygen and sulfur atoms; however, more preferably one is a nitrogen atom or an oxygen atom and the other is a nitrogen, oxygen or sulfur atom. Examples of such heterocyclic groups include the furyl, thienyl, pyrrolyl, oxazolyl, isoxazolyl, thiazolyl, isothiazolyl, imidazolyl, pyrazolyl, pyridyl, pyridazinyl, pyrimidinyl, indolyl, quinolyl and quinazolinyl groups. Of these, the furyl, thienyl, oxazolyl, isoxazolyl, thiazolyl, isothiazolyl and pyridyl groups are preferred, and the furyl, thienyl and pyridyl groups are most preferred. Such groups may be either unsubstituted or they may be substituted by at least one substituent selected from the group consisting of substituents (a), defined above and exemplified below, preferably the alkyl groups having from 1 to 6 carbon atoms. Where the group is substituted, there is no particular limitation on the number of substituents, except such as may be imposed by the number of substitutable positions or possibly by steric constraints, however, in general, from 1 to 3 substituents are preferred. More preferably the group has 1 substituent or is unsubstituted, and most preferably the group is unsubstituted.

Where substituent (a) or (b) is an alkyl group, this has from 1 to 6 carbon atoms and may be as exemplified above.

Where substituent (a) or (b) is a group of formula $-NR^aR^b$, each of $R^a$ and $R^b$, which may be the same or different, is a hydrogen atom or an alkyl group, and the alkyl group may be as exemplified above. Examples of such groups of formula $-NR^aR^b$ include the amino, methylamino, ethylamino, propylamino, isopropylamino, butylamino, isobutylamino, sec-butylamino, t-butylamino, pentylamino, isopentylamino, neopentylamino, hexylamino, isohexylamino, dimethylamino, diethylamino, N-ethyl-N-propylamino, dipropylamino, diisopropylamino, N-methyl-N-propylamino and N-methyl-N-butylamino groups, of which the amino group is preferred.

Where substituent (b) represents an alkoxy group having from 1 to 6 carbon atoms, this may be a straight or branched chain group having from 1 to 6 carbon atoms, and examples include the methoxy, ethoxy, propoxy, isopropoxy, butoxy, isobutoxy, sec-butoxy, t-butoxy, pentyl, isopentyloxy, neopentyloxy, 2-methylbutoxy, 1-ethylpropoxy, 4-methylpentyloxy, 3-methylpentyloxy, 2-methylpentyloxy, 1-methylpentyloxy, 3,3-dimethyl butoxy, 2,2-dimethylbutoxy, 1,1-dimethylbutoxy, 1,2-dimethylbutoxy, 1,3-dimethylbutoxy, 2,3-dimethylbutoxy, 2-ethylbutoxy, hexyloxy and isohexyloxy groups, of which we prefer those alkoxy groups having from 1 to 4 carbon atoms, especially the methoxy and ethoxy groups and most preferably the methoxy group.

Where substituent (b) represents a halogen atom, this may be, for example, a fluorine, chlorine, bromine or iodine atom, and is preferably a fluorine or chlorine atom.

Where A represents an alkylene group, this may be a straight or branched chain group having from 2 to 6 carbon atoms. Examples of such groups include the ethylene, propylene, trimethylene, tetramethylene, pentamethylene and hexamethylene groups, those alkylene groups containing from 2 to 4 carbon atoms being more preferred, and the ethylene group being most preferred. These alkylene groups may be unsubstituted or they may be substituted by at least one, and preferably only one, carboxy group.

Where A is a substituted alkylene group, the compound is an acid and can form salts and esters There is no particular restriction on the nature of these salts and esters, provided that, where they are intended for therapeutic use, they are pharmaceutically acceptable. Where they are intended for non-therapeutic uses, e.g. as intermediates in the preparation of other, and possibly more active, compounds, even this restriction does not apply. In the case of the esters, these are compounds of formula (I) in which the substituent on the group represented by A is an esterified carboxy group, for example an alkoxycarbonyl or aryloxycarbonyl group.

Where this substituent is an alkoxycarbonyl group, the alkoxy part has from 1 to 6 carbon atoms and may be a straight or branched chain group. Examples include the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl, isopentyloxycarbonyl, neopentyloxycarbonyl, 2-methyl-butoxycarbonyl, 1-ethylpropoxycarbonyl, 4-methylpentyloxycarbonyl, 3-methylpentyloxycarbonyl, 2-methylpentyloxycarbonyl, 1-methylpentyloxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl, 2,3-dimethylbutoxycarbonyl, 2-ethylbutoxycarbonyl, hexyloxycarbonyl and isohexyloxycarbonyl groups, of which we prefer those alkoxycarbonyl groups in which the alkyl part has from 1 to 4 carbon atoms, especially the methoxycarbonyl and ethoxycarbonyl groups. However, the unsubtituted alkylene groups are most preferred.

Where this substituent is an aryloxycarbonyl group, the aryl part has from 6 to 10, and preferably 6 or 10, carbon atoms, and may be unsubstituted or substituted, as defined above. Examples of such aryl groups forming a part of the aryloxycarbonyl group are as given above in relation to $R^2$ and $R^3$. The most preferred aryloxycarbonyl group is the phenoxycarbonyl group.

The compounds of the present invention in which A represents an alkylene group having a carboxy substituent or in which $R^2$ or $R^3$ represents an aralkyl or aryl group having a hydroxy substituent can also form salts with bases. Examples of such salts include: salts with an alkali metal, such as sodium, potassium or lithium; salts with an alkaline earth metal, such as barium or calcium; salts with another metal, such as magnesium or aluminum; organic base salts, such as a salt with dicyclohexylamine; and salts with a basic amino acid, such as lysine or arginine. Also, where the compound of the present invention contains a basic group in its molecule, it can form acid addition salts. Examples of such acid addition salts include: salts with mineral acids, especially hydrohalic acids (such as hydrofluoric acid, hydrobromic acid, hydroiodic acid or hydrochloric acid), nitric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid or citric acid; and salts with amino acids, such as glutamic acid or aspartic acid.

The compounds of the present invention necessarily contain several asymmetric carbon atoms in their molecules, at least in the heterocyclic ring, and can thus form optical isomers. Although these are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

A preferred class of compounds of the present invention are those compounds of formula (I) and salts thereof in which:

$R^1$ represents a hydrogen atom, an alkyl group having from 1 to 4 carbon atoms, a benzyl group or a phenethyl group;

$R^2$ and $R^3$ are independently selected from the group consisting of:

hydrogen atoms;

alkyl groups having from 1 to 4 carbon atoms; phenylalkyl groups in which the alkyl part has from 1 to 4 carbon atoms and the phenyl part is unsubstituted or is substituted by at least one substituent selected from the group consisting of alkyl groups having from 1 to 4 carbon atoms, alkoxy groups having from 1 to 4 carbon atoms, hydroxy groups, halogen atoms and nitro groups; naphthylmethyl groups;

phenyl groups which are unsubstituted or are substituted by at least one substituent selected from the group consisting of alkyl groups having from 1 to 4 carbon atoms, alkoxy groups having from 1 to 4 carbon atoms, hydroxy groups, halogen atoms and nitro groups;

naphthyl groups; and pyridyl, furyl, thienyl, oxazolyl, thiazolyl, isooxazolyl and isothiazolyl groups which are unsubstituted or are substituted by at least one substituent selected from the group consisting of alkyl groups having from 1 to 4 carbon atoms;

$R^4$ represents a hydrogen atom, an alkyl group having from 1 to 4 carbon atoms, a benzyl group or a phenethyl group; and A represents an alkylene group which has from 2 to 4 carbon atoms and which is unsubstituted or is substituted by at least one substituent selected from the group consisting of carboxy groups and alkoxycarbonyl groups in which the alkoxy part has from 1 to 4 carbon atoms.

A more preferred class of compounds of the present invention are those compounds of formula (I) and salts thereof in which:

$R^1$ represents a hydrogen atom, a methyl group or a benzyl group;

$R^2$ and $R^3$ are independently selected from the group consisting of:

hydrogen atoms;

methyl groups; benzyl and phenethyl groups which are unsubstituted or are substituted by at least one substituent selected from the group consisting of methyl groups, methoxy groups, fluorine atoms, chlorine atoms and hydroxy groups;

phenyl groups which are unsubstituted or are substituted by at least one substituent selected from the group consisting of methyl groups, methoxy groups, fluorine atoms, chlorine atoms and hydroxy groups; and pyridyl, furyl and thienyl groups;

$R^4$ represents a hydrogen atom, a methyl group or a benzyl group; and

A represents an alkylene group which has from 2 to 4 carbon atoms.

A still more preferred class of compounds of the present invention are those compounds of formula (I) and salts thereof in which:

W represents an oxygen atom or a sulfur atom and X represents a group of formula —NH— or X represents a sulfur atom and W represents a group of formula —NH—;

$R^2$ represents a hydrogen atom;

a benzyl group which is unsubstituted or is substituted by at least one substituent selected from the group consisting of methyl groups, methoxy groups and hydroxy groups; or a phenyl group which is unsubstituted or is substituted by at least one substituent selected from the group consisting of methyl groups, methoxy groups and hydroxy groups;

$R^3$ represents a hydrogen atom;

$R^4$ represents a hydrogen atom; and

A represents an alkylene group which has from 2 to 4 carbon atoms.

The most preferred class of compounds of the present invention are those compounds of formula (I) in which:

W represents an oxygen atom or a sulfur atom and X represents a group of formula —NH—;

$R^2$ represents a hydrogen atom;

a benzyl group;

a phenyl group which is unsubstituted or is substituted by at least one substituent selected from the group consisting of methyl groups and methoxy groups;

$R^3$ represents a hydrogen atom;

$R^4$ represents a hydrogen atom; and

A represents an ethylene group.

Specific examples of individual compounds of the present invention are those compounds of formulae (Ia) and (Ib), shown above, in which A, $R^2$, $R^3$, $R^4$ and $X^1$ are as defined in Table 1 or Table 2, respectively, i.e. Table 1 relates to formula (Ia), and Table 2 relates to formula (Ib). In the Tables, the following abbreviations are used to identify certain groups:

| | |
|---|---|
| Bu | butyl |
| Bz | benzyl |
| Et | ethyl |
| Me | methyl |
| Ph | phenyl |
| Pr | propyl |

TABLE 1

| Cpd. No. | R¹ | R² | R³ | R⁴ | A | X¹ |
| --- | --- | --- | --- | --- | --- | --- |
| 1-1 | H | H | H | H | (CH₂)₂ | S |
| 1-2 | Me | H | H | H | (CH₂)₂ | S |
| 1-3 | Et | H | H | H | (CH₂)₂ | S |
| 1-4 | Bz | H | H | H | (CH₂)₂ | S |
| 1-5 | H | Me | H | H | (CH₂)₂ | S |
| 1-6 | H | Et | H | H | (CH₂)₂ | S |
| 1-7 | H | Ph | H | H | (CH₂)₂ | S |
| 1-8 | H | 2-Thienyl | H | H | (CH₂)₂ | S |
| 1-9 | H | 3-Thienyl | H | H | (CH₂)₂ | S |
| 1-10 | H | 2-Furyl | H | H | (CH₂)₂ | S |
| 1-11 | H | 3-Furyl | H | H | (CH₂)₂ | S |
| 1-12 | H | 3-NO₂—Ph | H | H | (CH₂)₂ | S |
| 1-13 | H | 4-Cl—Ph | H | H | (CH₂)₂ | S |
| 1-14 | H | 4-MeO—Ph | H | H | (CH₂)₂ | S |
| 1-15 | H | 4-Thiazolyl | H | H | (CH₂)₂ | S |
| 1-16 | H | 3-Pyridyl | H | H | (CH₂)₂ | S |
| 1-17 | H | Me | Me | H | (CH₂)₂ | S |
| 1-18 | Me | Me | Me | H | (CH₂)₂ | S |
| 1-19 | Me | Me | Me | Me | (CH₂)₂ | S |
| 1-20 | Et | Ph | H | H | (CH₂)₃ | S |
| 1-21 | Et | Et | H | Me | (CH₂)₄ | S |
| 1-22 | Bz | Me | H | Et | (CH₂)₂ | S |
| 1-23 | Bz | Ph | H | Pr | (CH₂)₄ | S |
| 1-24 | Bu | H | H | H | (CH₂)₂ | S |
| 1-25 | H | 1-Naphthyl | H | H | (CH₂)₂ | S |
| 1-26 | H | H | H | Me | (CH₂)₂ | S |
| 1-27 | H | H | H | Bz | (CH₂)₂ | S |
| 1-28 | H | Bz | H | H | (CH₂)₂ | S |
| 1-29 | Bz | H | H | H | (CH₂)₃ | S |
| 1-30 | H | H | H | H | CH(Me)CH₂ | S |
| 1-31 | H | H | H | H | CH₂CH(Me) | S |
| 1-32 | H | H | H | H | (CH₂)₅ | S |
| 1-33 | H | H | H | H | (CH₂)₆ | S |
| 1-34 | H | H | H | H | (CH₂)₂ | O |
| 1-35 | Me | H | H | H | (CH₂)₂ | O |
| 1-36 | Et | H | H | H | (CH₂)₂ | O |
| 1-37 | Bz | H | H | H | (CH₂)₂ | O |
| 1-38 | H | Me | H | H | (CH₂)₂ | O |
| 1-39 | H | Et | H | H | (CH₂)₂ | O |
| 1-40 | H | Ph | H | H | (CH₂)₂ | O |
| 1-41 | H | 2-Thienyl | H | H | (CH₂)₂ | O |
| 1-42 | H | 3-Thienyl | H | H | (CH₂)₂ | O |
| 1-43 | H | 2-Furyl | H | H | (CH₂)₂ | O |
| 1-44 | H | 3-Furyl | H | H | (CH₂)₂ | O |
| 1-45 | H | 3-NO₂—Ph | H | H | (CH₂)₂ | O |
| 1-46 | H | 4-Cl—Ph | H | H | (CH₂)₂ | O |
| 1-47 | H | 4-MeO—Ph | H | H | (CH₂)₂ | O |
| 1-48 | H | 4-Thiazolyl | H | H | (CH₂)₂ | O |
| 1-49 | H | 3-Pyridyl | H | H | (CH₂)₂ | O |
| 1-50 | H | Me | Me | H | (CH₂)₂ | O |
| 1-51 | Me | Me | Me | H | (CH₂)₂ | O |
| 1-52 | Me | Me | Me | Me | (CH₂)₂ | O |
| 1-53 | Et | Ph | H | H | (CH₂)₃ | O |
| 1-54 | Et | Et | H | Me | (CH₂)₄ | O |
| 1-55 | Bz | Me | H | Et | (CH₂)₂ | O |
| 1-56 | Bz | Ph | H | Pr | (CH₂)₄ | O |
| 1-57 | Bu | H | H | H | (CH₂)₂ | O |
| 1-58 | H | 1-Naphthyl | H | H | (CH₂)₂ | O |
| 1-59 | H | H | H | Me | (CH₂)₂ | O |
| 1-60 | H | H | H | Bz | (CH₂)₂ | O |
| 1-61 | H | Bz | H | H | (CH₂)₂ | O |
| 1-62 | H | H | H | H | (CH₂)₃ | O |
| 1-63 | H | H | H | H | CH(Me)CH₂ | O |
| 1-64 | H | H | H | H | CH₂CH(Me) | O |
| 1-65 | H | H | H | H | (CH₂)₅ | O |
| 1-66 | H | H | H | H | (CH₂)₆ | O |
| 1-67 | H | H | H | H | (CH₂)₄ | S |
| 1-68 | H | H | H | H | (CH₂)₃ | S |
| 1-69 | H | 4-Me—Bz | H | H | (CH₂)₂ | S |
| 1-70 | H | 4-MeO—Bz | H | H | (CH₂)₂ | S |
| 1-71 | H | 4-F—Bz | H | H | (CH₂)₂ | S |
| 1-72 | H | 4-Cl—Bz | H | H | (CH₂)₂ | S |
| 1-73 | H | 4-OH—Bz | H | H | (CH₂)₂ | S |
| 1-74 | H | 4-Me—Ph | H | H | (CH₂)₂ | S |
| 1-75 | H | 4-F—Bz | H | H | (CH₂)₂ | S |
| 1-76 | H | 4-OH—Ph | H | H | (CH₂)₂ | S |
| 1-77 | H | 4-Me—Bz | H | H | (CH₂)₂ | O |
| 1-78 | H | 4-OMe—Bz | H | H | (CH₂)₂ | O |
| 1-79 | H | 4-F—Bz | H | H | (CH₂)₂ | O |
| 1-80 | H | 4-Cl—Bz | H | H | (CH₂)₂ | O |
| 1-81 | H | 4-OH—Bz | H | H | (CH₂)₂ | O |
| 1-82 | H | 4-Me—Ph | H | H | (CH₂)₂ | O |
| 1-83 | H | 4-F—Ph | H | H | (CH₂)₂ | O |
| 1-84 | H | 4-OH—Ph | H | H | (CH₂)₂ | O |
| 1-85 | H | H | H | H | (CH₂)₄ | O |

TABLE 2

| Cpd. No. | R¹ | R² | R³ | R⁴ | A | X¹ |
| --- | --- | --- | --- | --- | --- | --- |
| 2-1 | H | H | H | H | (CH₂)₂ | S |
| 2-2 | Me | H | H | H | (CH₂)₂ | S |
| 2-3 | Et | H | H | H | (CH₂)₂ | S |
| 2-4 | Bz | H | H | H | (CH₂)₂ | S |
| 2-5 | H | Me | H | H | (CH₂)₂ | S |
| 2-6 | H | Et | H | H | (CH₂)₂ | S |
| 2-7 | H | Ph | H | H | (CH₂)₂ | S |
| 2-8 | H | 2-Thienyl | H | H | (CH₂)₂ | S |
| 2-9 | H | 3-Thienyl | H | H | (CH₂)₂ | S |
| 2-10 | H | 2-Furyl | H | H | (CH₂)₂ | S |
| 2-11 | H | 3-Furyl | H | H | (CH₂)₂ | S |
| 2-12 | H | 3-NO₂—Ph | H | H | (CH₂)₂ | S |
| 2-13 | H | 4-Cl—Ph | H | H | (CH₂)₂ | S |
| 2-14 | H | 4-MeO—Ph | H | H | (CH₂)₂ | S |
| 2-15 | H | 4-Thiazolyl | H | H | (CH₂)₂ | S |
| 2-16 | H | 3-Pyridyl | H | H | (CH₂)₂ | S |
| 2-17 | H | Me | Me | H | (CH₂)₂ | S |
| 2-18 | Me | Me | Me | H | (CH₂)₂ | S |
| 2-19 | Me | Me | Me | Me | (CH₂)₂ | S |
| 2-20 | Et | Ph | H | H | (CH₂)₃ | S |
| 2-21 | Et | Et | H | Me | (CH₂)₄ | S |
| 2-22 | Bz | Me | H | Et | (CH₂)₂ | S |
| 2-23 | Bz | Ph | H | Pr | (CH₂)₄ | S |
| 2-24 | Bu | H | H | H | (CH₂)₂ | S |
| 2-25 | H | 1-Naphthyl | H | H | (CH₂)₂ | S |
| 2-26 | H | H | H | Me | (CH₂)₂ | S |
| 2-27 | H | H | H | Bz | (CH₂)₂ | S |
| 2-28 | H | Bz | H | H | (CH₂)₂ | S |
| 2-29 | H | H | H | H | (CH₂)₃ | S |
| 2-30 | H | H | H | H | CH(Me)CH₂ | S |
| 2-31 | H | H | H | H | CH₂CH(Me) | S |
| 2-32 | H | H | H | H | (CH₂)₅ | S |
| 2-33 | H | H | H | H | (CH₂)₆ | S |
| 2-34 | H | H | H | H | (CH₂)₂ | O |
| 2-35 | Me | H | H | H | (CH₂)₂ | O |
| 2-36 | Et | H | H | H | (CH₂)₂ | O |
| 2-37 | Bz | H | H | H | (CH₂)₂ | O |
| 2-38 | H | Me | H | H | (CH₂)₂ | O |
| 2-39 | H | Et | H | H | (CH₂)₂ | O |
| 2-40 | H | Ph | H | H | (CH₂)₂ | O |
| 2-41 | H | 2-Thienyl | H | H | (CH₂)₂ | O |
| 2-42 | H | 3-Thienyl | H | H | (CH₂)₂ | O |
| 2-43 | H | 2-Furyl | H | H | (CH₂)₂ | O |
| 2-44 | H | 3-Furyl | H | H | (CH₂)₂ | O |
| 2-45 | H | 3-NO₂—Ph | H | H | (CH₂)₂ | O |
| 2-46 | H | 4-Cl—Ph | H | H | (CH₂)₂ | O |
| 2-47 | H | 4-MeO—Ph | H | H | (CH₂)₂ | O |
| 2-48 | H | 4-Thiazolyl | H | H | (CH₂)₂ | O |
| 2-49 | H | 3-Pyridyl | H | H | (CH₂)₂ | O |
| 2-50 | H | Me | Me | H | (CH₂)₂ | O |
| 2-51 | Me | Me | Me | H | (CH₂)₂ | O |
| 2-52 | Me | Me | Me | Me | (CH₂)₂ | O |
| 2-53 | Et | Ph | H | H | (CH₂)₃ | O |
| 2-54 | Et | Et | H | Me | (CH₂)₄ | O |
| 2-55 | Bz | Me | H | Et | (CH₂)₂ | O |
| 2-56 | Bz | Ph | H | Pr | (CH₂)₄ | O |
| 2-57 | Bu | H | H | H | (CH₂)₂ | O |
| 2-58 | H | 1-Naphthyl | H | H | (CH₂)₂ | O |
| 2-59 | H | H | H | Me | (CH₂)₂ | O |
| 2-60 | H | H | H | Bz | (CH₂)₂ | O |
| 2-61 | H | Bz | H | H | (CH₂)₂ | O |
| 2-62 | H | H | H | H | (CH₂)₃ | O |
| 2-63 | H | H | H | H | CH(Me)CH₂ | O |
| 2-64 | H | H | H | H | CH₂CH(Me) | O |
| 2-65 | H | 4-Me—Ph | H | H | (CH₂)₂ | O |
| 2-66 | H | 4-Me—Ph | H | H | (CH₂)₂ | S |
| 2-67 | H | 4-Me—Bz | H | H | (CH₂)₂ | S |
| 2-68 | H | 4-MeO—Bz | H | H | (CH₂)₂ | S |

TABLE 2-continued

| Cpd. No. | $R^1$ | $R^2$ | $R^3$ | $R^4$ | A | $X^1$ |
|---|---|---|---|---|---|---|
| 2-69 | H | 4-F—Bz | H | H | $(CH_2)_2$ | S |
| 2-70 | H | 4-Cl—Bz | H | H | $(CH_2)_2$ | S |
| 2-71 | H | 4-OH—Bz | H | H | $(CH_2)_2$ | S |
| 2-72 | H | 4-F—Ph | H | H | $(CH_2)_2$ | S |
| 2-73 | H | 4-OH—Ph | H | H | $(CH_2)_2$ | S |
| 2-74 | H | 4-Me—Bz | H | H | $(CH_2)_2$ | O |
| 2-75 | H | 4-OMe—Bz | H | H | $(CH_2)_2$ | O |
| 2-76 | H | 4-F—Bz | H | H | $(CH_2)_2$ | O |
| 2-77 | H | 4-Cl—Bz | H | H | $(CH_2)_2$ | O |
| 2-78 | H | 4-OH—Bz | H | H | $(CH_2)_2$ | O |
| 2-79 | H | 4-F—Ph | H | H | $(CH_2)_2$ | O |
| 2-80 | H | 4-OH—Ph | H | H | $(CH_2)_2$ | O |
| 2-81 | H | H | H | H | $(CH_2)_4$ | S |
| 2-82 | H | H | H | H | $(CH_2)_4$ | O |

Of the compound listed above, the preferred compounds are Compounds No. 1-1, 1-2, 1-5, 1-7, 1-8, 1-9, 1-10, 1-11, 1-12, 1-13, 1-14, 1-16, 1-17, 1-25, 1-26, 1-28, 1-30, 1-31, 1-34, 1-35, 1-38, 1-40, 1-41, 1-42, 1-43, 1-44, 1-47, 1-61, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 2-1, 2-5, 2-7, 2-14, 2-34, 2-38, 2-40, 2-47, 2-65, 2-66, 2-67, 2-68, 2-69, 2-70, 2-71, 2-72 and 2-73, and the more preferred compounds are Compounds No. 1-1, 1-2, 1-5, 1-7, 1-8, 1-14, 1-25, 1-28, 1-30, 1-34, 1-38, 1-41, 1-47, 1-61, 1-69, 1-70, 1-74, 1-78, 2-1, 2-7, 2-14, 2-66, 2-67 and 2-68. The most preferred compounds are Compounds No.:

1-1. N-(2-Nitrooxyethyl)-2-oxothiazolidine-4-carboxamide;

1-14. N-(2-Nitrooxyethyl)-5-(4-methoxyphenyl)-2-oxothiazolidine-4-carboxamide;

1-28. N-(2-Nitrooxyethyl)-5-benzyl-2-oxothiazolidine-4-carboxamide;

1-34. N-(2-Nitrooxyethyl)-2-oxooxazolidine-4-carboxamide;

1-47. N-(2-Nitrooxyethyl)-5-(4-methoxyphenyl)-2-oxo-oxazolidine-4-carboxamide;

1-61. N-(2-Nitrooxyethyl)-5-benzyl-2-oxooxazolidine-4-carboxamide;

2-1. N-(2-Nitrooxyethyl)-2-oxothiazolidine-5-carboxamide; and 2-14. N-(2-Nitrooxyethyl)-4-(4-methoxyphenyl)-2-oxothiazolidine-5-carboxamide.

The compounds of the present invention can be prepared by a variety of methods well known in the art for the preparation of compounds of this type. For example, in general teams, they may be prepared by reacting a compound of formula (II):

$$O=\underset{X}{\overset{W}{\diagup}}\overset{R^2}{\underset{COOH}{\diagdown}}R^3 \quad (II)$$

in which W, X, $R^2$ and $R^3$ are as defined above) or an active derivative thereof with a compound of formula (III):

$$\underset{R^4}{\overset{HN-A-OZ}{|}} \quad (III)$$

(in which $R^4$ and A are as defined above and Z represents a hydrogen atom or a nitro group) to give a compound of formula (IV):

$$O=\underset{X}{\overset{W}{\diagup}}\overset{R^2}{\underset{CO-N-A-OZ}{\diagdown}}R^3 \quad (IV)$$
$$\underset{R^4}{|}$$

(in which W, X, $R^2$, $R^3$, $R^4$, A and Z are as defined above);

and, where Z represents a hydrogen atom, nitrating the compound of formula (IV), to give a compound of formula (I);

and optionally salifying or esterifying the product.

In more detail, the compounds of the present invention can be prepared as illustrated in the following Reaction Schemes A and B:

Reaction Scheme A:

$$O=\underset{X}{\overset{W}{\diagup}}\overset{R^2}{\underset{COOH}{\diagdown}}R^3 \quad + \quad \underset{R^4}{\overset{HN-A-ONO_2}{|}} \quad \xrightarrow{\text{Step A1}}$$

(II)　　　　　　　　(IIIa)

$$O=\underset{X}{\overset{W}{\diagup}}\overset{R^2}{\underset{CO-N-A-ONO_2}{\diagdown}}R^3$$
$$\underset{R^4}{|}$$

(I)

Reaction Scheme B:

$$O=\underset{X}{\overset{W}{\diagup}}\overset{R^2}{\underset{COOH}{\diagdown}}R^3 \quad + \quad \underset{R^4}{\overset{HN-A-OH}{|}} \quad \xrightarrow{\text{Step B1}}$$

(II)　　　　　　　　(IIIb)

$$O=\underset{X}{\overset{W}{\diagup}}\overset{R^2}{\underset{CO-N-A-OH}{\diagdown}}R^3 \quad \xrightarrow{\text{Step B2}}$$
$$\underset{R^4}{|}$$

(IVa)

$$O=\underset{X}{\overset{W}{\diagup}}\overset{R^2}{\underset{CO-N-A-ONO_2}{\diagdown}}R^3$$
$$\underset{R^4}{|}$$

(I)

In the above formulae, W, X, $R^2$, $R^3$, $R^4$ and A are as defined above.

In Step A1 of this Reaction Scheme, the compound of formula (I) is prepared by reacting a compound of formula (II) or a reactive derivative thereof with a compound of formula (IIIa). The reactive derivative may be, for example, an acid halide, a mixed acid anhydride or an activated ester; alternatively, the reaction may be carried out using the free acid in the presence of a condensing agent.

When an acid halide of the compound of formula (II) is used (the "acid halide method"), the compound of formula (II) is first reacted with a halogenating agent (for example thionyl chloride or phosphorus pentachloride), to produce an acid halide, and then this acid halide is reacted with a compound of formula (IIIa). The reaction may be effected in the presence or absence of a base.

There is no particular restriction on the nature of the base used, provided that it has no adverse effect on the reagents. Examples of bases which may be used include: organic amines, such as triethylamine, N-methylmorpholine, pyridine or 4-dimethylaminopyridine; alkali metal hydrogencarbonates, such as sodium hydrogencarbonate or potassium hydrogencarbonate; and alkali metal carbonates, such as sodium carbonate or potassium carbonate. Of these, we prefer the organic amines.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic, cycloaliphatic or aromatic, such as hexane, cyclohexane, benzene, toluene or xylene; halogenated hydrocarbons, preferably halogenated aliphatic hydrocarbons, such as methylene chloride, 1,2-dichloroethane or carbon tetrachloride; ethers, such as diethyl ether, tetrahydrofuran or dioxane; ketones, such as acetone; amides, especially fatty acid amides, such as N,N-dimethylformamide, N,N-dimethylacetamide, N-methyl-2-pyrrolidone or hexamethylphosphoric triamide; and sulfoxides, such as dimethyl sulfoxide. Of these, we prefer the hydrocarbons, halogenated hydrocarbons, ethers and amides.

These reactions can take place over a wide range of temperatures, and the precise reaction temperature is not critical to the invention. In general, we find it convenient to carry out the reaction at a temperature of from −20° C. to 150° C. for both the reaction of the compound of formula (II) with the halogenating agent and the reaction of the compound of formula (IIIa) with the acid halide; more preferably the reaction of the compound of formula (II) with the halogenating agent is conducted at from −10° C. to 50° C. and the reaction of the compound of formula (IIIa) with the acid halide is conducted at a temperature of from 0° C. to 100° C. The time required for the reactions may also vary widely, depending on many factors, notably the reaction temperature and the nature of the reagents and solvent employed. However, provided that the reaction is effected under the preferred conditions outlined above, a period of from 15 minutes to 24 hours, more preferably from 30 minutes to 16 hours, will usually suffice for each reaction.

The mixed acid anhydride method may be carried out by reacting the compound of formula (II) with an alkyl halocarbonate (in which the alkyl group has from 1 to 4 carbon atoms), a dialkyl cyanophosphonate (in which each alkyl group has from 1 to 4 carbon atoms) or a diarylphosphoryl azide (in which each aryl group is as defined above in relation to $R^2$ and $R^3$), to produce a mixed acid anhydride and then reacting the product with a compound of formula (IIIa).

The preparation of the mixed acid anhydride may be carried out by reacting the compound of formula (II) with an alkyl halocarbonate, such as ethyl chloroformate or isobutyl chloroformate, a dialkyl cyanophosphonate, such as dimethyl cyanophosphonate or diethyl cyanophosphonate, or a diarylphosphoryl azide, such as diphenylphosphoryl azide, di(p-nitrophenyl)phosphoryl azide or dinaphthylphosphoryl azide. The reaction is preferably carried out in an inert solvent and preferably in the presence of a base.

There is no particular restriction on the nature of the bases and inert solvents which may be used in this reaction, and they are similar to those which may be used, as described above, in the acid halide method.

The reaction can take place over a wide range of temperatures, and the precise reaction temperature is not critical to the invention. In general, we find it convenient to carry out the reaction at a temperature of from −20° C. to 50° C., more preferably from 0° C. to 30° C. The time required for the reaction may also vary widely, depending on many factors, notably the reaction temperature and the nature of the reagents and solvent employed. However, provided that the reaction is effected under the preferred conditions outlined above, a period of from 15 minutes to 24 hours, more preferably from 30 minutes to 16 hours, will usually suffice.

Reaction of the compound of formula (IIIa) with the resulting mixed acid anhydride is preferably carried out in an inert solvent and may be carried out in the presence or absence of a base. There is no particular restriction on the nature of the bases and inert solvents which may be used in this reaction, and they are similar to those which may be used, as described above, in the acid halide method.

The reaction can take place over a wide range of temperatures, and the precise reaction temperature is not critical to the invention. In general, we find it convenient to carry out the reaction at a temperature of from −20° C. to 100° C., more preferably from −10° C. to 50° C. The time required for the reaction may also vary widely, depending on many factors, notably the reaction temperature and the nature of the reagents and solvent employed. However, provided that the reaction is effected under the preferred conditions outlined above, a period of from 15 minutes to 24 hours, more preferably from 30 minutes to 16 hours, will usually suffice.

In this method, when a dialkyl cyanophosphonate or a diarylphosphoryl azide is used as a reagent, the reaction of the compound of formula (II) may preferably be carried out with the compound of formula (IIIa) in the reaction system, and in the presence of a base.

The activated ester method can be carried out by reacting the compound of formula (II) in the presence of a condensing agent (for example, dicyclohexylcarbodiimide or carbonyldiimidazole) with an active esterifying agent (for example, an N-hydroxy compound, such as N-hydroxysuccinimide or N-hydroxybenzotriazole), to produce an activated ester compound and then reacting the product with a compound of formula (IIIa).

The reaction used to prepare the activated ester compound is preferably conducted in an inert solvent and the solvents which may be used in the reaction are similar to those used, as described above, in the acid halide method.

These reactions can take place over a wide range of temperatures, and the precise reaction temperature is not critical to the invention. In general, we find it convenient to carry out the reaction for preparing the activated ester compound at a temperature of from $-20°$ C. to 50° C., more preferably from $-10°$ C. to 30° C., and the reaction of the activated ester compound with the compound of formula (IIIa) is preferably carried out at a temperature of from $-20°$ C. to 50° C., more preferably from $-10°$ C. to 30° C. The time required for the reactions may also vary widely, depending on many factors, notably the reaction temperature and the nature of the reagents and solvent employed. However, provided that the reaction is effected under the preferred conditions outlined above, a period of from 15 minutes to 24 hours, more preferably from 30 minutes to 16 hours, will usually suffice for each of the reactions.

The condensing method is carried out by reacting the compound of formula (II) with the compound of formula (IIIa) directly in the presence of a condensing agent, for example, dicyclohexylcarbodiimide, carbonyldiimidazole or 1-(N,N-dimethylaminopropyl)-3-ethylcarbodiimide hydrochloride. The reaction conditions employed in this method are similar to those employed, as described above, in the activated ester method.

Where the compound of formula (II) contains an amino group or a monoalkylamino group and the compound of formula (IIIa) contains a carboxy group, it is preferred to use a compound in which these groups are protected. There is no particular limitation upon the nature of the protecting group, and any such group commonly used in organic synthetic chemistry may equally be used in this reaction. Examples of suitable amino- or monoalkylamino- protecting groups include the t-butoxycarbonyl and haloacetyl groups, for example the chloroacetyl, bromoacetyl or iodoacetyl groups. Examples of carboxy-protecting groups include: the t-butyl group and alkoxybenzyl groups in which the alkoxy part has from 1 to 4 carbon atoms, such as the p-methoxybenzyl group.

The protecting group can be removed, after completion of the above reaction, by conventional means well known in the field of organic synthetic chemistry, the exact method chosen depending upon the nature of the protecting group.

For example, where the protecting group is a t-butoxycarbonyl, t-butyl or alkoxybenzyl group, it can be removed by reacting the protected compound in an inert solvent (for example, an ether, such as diethyl ether, tetrahydrofuran or dioxane; a halogenated hydrocarbon, such as methylene chloride or 1,2-dichloroethane; or an aromatic hydrocarbon, such as benzene, toluene or xylene) with an acid (for example, a mineral acid, such as hydrochloric acid, sulfuric acid or nitric acid; or an organic acid, such as acetic acid, trifluoroacetic acid, methanesulfonic acid or p-toluenesulfonic acid) at a temperature of from 0° C. to 50° C. (more preferably at about room temperature) for a period of from 30 minutes to 5 hours (more preferably from 1 to 2 hours). Where the protecting group is a haloacetyl group, it can be removed by reacting the protected compound in an inert solvent (for example, an amide, such as dimethylformamide or dimethylacetamide; or a sulfoxide, such as dimethyl sulfoxide) with thiourea at a temperature of from 0° C. to 50° C. (more preferably at about room temperature) for a period of from 30 minutes to 5 hours (more preferably from 1 to 2 hours).

After completion of the reaction, the desired compound produced by each reaction can be recovered from the reaction mixture by conventional means. For example, in appropriate cases, the desired compound can be recovered by collecting precipitated crystals by filtration. Alternatively, it can be recovered by diluting the reaction mixture with water and then extracting it with a water-immiscible solvent, such as ethyl acetate; the extract is then dried, and finally the solvent is removed, e.g. by distillation under reduced pressure. The product can, if necessary, be further purified by conventional means, for example, by recrystallization, or by the various chromatography techniques, notably column chromatography or preparative thin layer chromatography.

The compounds of formula (II) used as starting materials in Method A are well known or can readily be prepared by known methods [for example, as described in Aust. J. Chem., 21, 1891(1968), J. Chem. Soc., 4614 (1958), J. Pharm. Soc. Japan, 73, 949 (1953), Chem. Berichte, 91, 160(1958) and J. Chem. Soc. Japan, 82, 1075(1961)].

Reaction Scheme B provides an alternative method of preparing the compounds of formula (I).

In Step B1 of Reaction Scheme a compound of formula (IVa) is prepared by reacting a compound of formula (II) or a reactive derivative thereof with a hydroxy compound of formula (IIIb). The reaction can be carried out using, for example, the acid halide, mixed acid anhydride, activated ester or condensing method, all as described above in relation to Step A1 of Reaction Scheme A.

In Step B2, the compound of formula (I) is prepared by reacting the hydroxy compound of formula (IVa), prepared in Step B1, with a nitrating agent, either in the absence of a solvent or in an inert solvent.

There is no particular restriction on the nature of the nitrating agent used, and examples include fuming nitric acid, nitrocollidinium tetrafluoroborate, thionyl chloride nitrate, thionyl nitrate and nitronium tetrafluoroborate. Of these, we prefer fuming nitric acid, nitrocollidinium tetrafluoroborate or thionyl chloride nitrate.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic, cycloaliphatic or aromatic, such as hexane, cyclohexane, benzene, toluene or xylene; halogenated hydrocarbons, especially halogenated aliphatic hydrocarbons such as methylene chloride, 1,2-dichloroethane or carbon tetrachloride; ethers, such as diethyl ether, tetrahydrofuran or dioxane; ketones, such as acetone; nitriles, such as acetonitrile; amides, especially fatty acid amides, such as N,N-dimethylformamide, N,N-dimethylacetamide, N-methyl-2-pyrrolidone or hexamethylphosphoric triamide; and sulfoxides, such as dimethyl sulfoxide. Of these, we prefer the hydrocarbons, halogenated hydrocarbons, ethers, amides and sulfoxides.

The reaction can take place over a wide range of temperatures, and the precise reaction temperature is not critical to the invention. In general, we find it convenient to carry out the reaction at a temperature of from −20° C. to 50° C., more preferably at about room temperature. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 10 hours, will usually suffice.

After completion of the reaction, the desired compound can be recovered from the reaction mixture by conventional means. For example, in appropriate cases, the desired compound can be recovered by collecting precipitated crystals by filtration. Alternatively, it may be recovered by adding water, extracting the mixture with a water-immiscible solvent, such as ethyl acetate, drying the extract and finally distilling off the solvent under reduced pressure. The product can, if necessary, be further purified by conventional means, for example, by recrystallization, or by the various chromatography techniques, notably column chromatography or preparative thin layer chromatography.

As is demonstrated hereafter, the compounds of the present invention may be used for the treatment and prophylaxis of angina pectoris. For this purpose, they may be administered alone or in admixture with conventional pharmaceutically acceptable carriers, diluents, excipients or adjuvants, as is well known in the art. They may be administered by any desired route, for example orally or parenterally. If desired, they may be formulated as any formulation suitable for the intended route of administration, for example they may be in the form of powders, granules, tablets or capsules for oral administration, or in the form of an injection for parenteral administration. The dosage may vary depending upon the severity and nature of the disorder, as well as the symptoms, age and body weight of the patient and the chosen route of administration; however, in the case of oral administration, we would normally suggest a single dose of from 1 to 1000 mg, particularly from 5 to 300 mg; and, in the case of intravenous injection, a single dose of from 0.1 to 100 mg, particularly from 0.5 to 50 mg. This may be administered one or more times per day, for example from once to three times a day.

The preparation of the compounds of the present invention is further illustrated by the following non-limiting Examples, whilst the preparation of certain of the starting materials used in these Examples is illustrated by the subsequent Preparations. Biological activity of some of the compounds of the present invention is then demonstrated.

EXAMPLE 1

(4R)-N-(2-Nitrooxyethyl)-2-oxothiazolidine-4-carboxamide (Compound No. 1-1)

11.4 ml of triethylamine and 5.3 ml of diethyl cyanophosphonate were added, whilst ice-cooling, to a suspension of 4.0 g of (4R)-2-oxothiazolidine-4-carboxylic acid and 4.6 g of N-(2-nitrooxyethyl)amine nitrate in 80 ml of dry tetrahydrofuran, and the resulting mixture was stirred at room temperature for 2 hours. At the end of this time, the solvent was removed by distillation under reduced pressure, and the residue was mixed with ethyl acetate. The resulting mixture was then washed with a saturated aqueous solution of sodium chloride, after which it was dried over anhydrous magnesium sulfate. The solvent was then removed by distillation under reduced pressure, and the residual brown oil thus obtained was purified by column chromatography through silica gel, using ethyl acetate as the eluent. The brown crystals thus obtained were recrystallized from ethyl acetate, to give 1.68 g of the title compound as colorless needles, melting at 130°–131° C. (with decomposition).

Nuclear Magnetic Resonance Spectrum (CDCl$_3$ + hexadeuterated dimethyl sulfoxide) δ ppm:
3.54–3.73 (4H, multiplet);
4.31 (1H, triplet, J=7 Hz);
4.58 (2H, triplet, J=5 Hz);
7.81 (1H, singlet);
8.02 (1H, broad singlet).

EXAMPLE 2

(4R,5R)-N-(2-Nitrooxyethyl)-2-oxo-5-methylthiazolidine-4-carboxamide (Compound No. 1-5)

1.33 ml of triethylamine and 0.36 ml of diethyl cyanophosphonate were added, whilst ice-cooling and stirring, to a suspension of 322 mg of (4R,5R)-5-methyl-2-oxothiazolidine-4-carboxylic acid and 406 mg of N-(2-nitrooxyethyl)amine nitrate in 40 ml of dry tetrahydrofuran, and the resulting mixture was stirred at room temperature for 1 hour and 25 minutes. At the end of this time, the solvent was removed by distillation under reduced pressure, and the residue was mixed with ethyl acetate. The resulting mixture was washed with a saturated aqueous solution of sodium chloride and then dried over anhydrous magnesium sulfate. The solvent was removed by distillation under reduced pressure, and the residual yellow oil thus obtained was purified by column chromatography through silica gel, using a 20:1 by volume mixture of methylene chloride and methanol as the eluent, to give 324 mg of the title compound as a pale yellow oil.

Nuclear Magnetic Resonance Spectrum (CDCl$_3$) δ ppm:
1.61 (3H, doublet, J=6 Hz);
3.55–3.77 (2H, multiplet);
4.04 (2H, broad singlet);
4.59 (2H, triplet, J=5 Hz);
7.61 (1H, singlet);
7.73 (1H, triplet, J=6 Hz).

EXAMPLE 3

N-(2-Nitrooxyethyl)-2-oxo-5-phenylthiazolidine-4-carboxamide (Compound No. 1-7)

0.07 ml of triethylamine and 90 mg of 1-(N,N-dimethylaminopropyl)-3-ethylcarbodiimide hydrochloride were added, whilst ice-cooling and stirring, to a solution of 105 mg of 2-oxo-5-phenylthiazolidine-4-carboxylic acid and 79.5 mg of N-(2-nitrooxyethyl)amine nitrate in 10 ml of dry N,N-dimethylformamide, and the resulting mixture was stirred at room temperature overnight. At the end of this time, the solvent was removed by distillation under reduced pressure, and the residue was mixed with ethyl acetate. The resulting mixture was washed with a saturated aqueous solution of sodium chloride and then dried over anhydrous magnesium sulfate. The solvent was distilled off and the residual yellow oil was triturated with diethyl ether. The crystals which precipitated were collected by filtration and purified by column chromatography through silica gel, using a 40:1 by volume mixture of methylene chloride and methanol as the eluent, to give 34 mg of the title compound as pale yellow crystals, melting at 139°–140° C.

Nuclear Magnetic Resonance Spectrum (CDCl$_3$+hexadeuterated dimethyl sulfoxide) δ ppm:
- 3.62–3.80 (2H, multiplet);
- 4.28 (1H, doublet, J=4 Hz);
- 4.58 (1H, triplet, J=5Hz);
- 5.24 (2H, broad singlet);
- 7.32–7.52 (5H, multiplet);
- 7.64 (1H, broad singlet).

EXAMPLE 4

N-(2-Nitrooxyethyl)-5,5-dimethyl-2-oxothiazolidine-4-carboxamide (Compound No. 1-17)

1.38 ml of triethylamine and 0.37 ml of diethyl cyanophosphonate were added, whilst ice-cooling and stirring, to a suspension of 360 mg of 5,5-dimethyl-2-oxothiazolidine-4-carboxylic acid and 417 mg of N-(2-nitrooxyethyl)amine nitrate in 50 ml of dry tetrahydrofuran, and the resulting mixture was stirred at room temperature for 4 hours, after which the solvent was removed by distillation under reduced pressure. The residue was mixed with ethyl acetate, and the resulting mixture was washed with a saturated aqueous solution of sodium chloride and dried over anhydrous magnesium sulfate. The solvent was then removed by distillation under reduced pressure. The residual pale yellow oil was purified by column chromatography through silica gel, using a 50:1 by volume mixture of methylene chloride and methanol as the eluent. The crystals thus obtained were recrystallized from diethyl ether, to give 180 mg of the title compound as colorless crystals, melting at 98°–100° C.

Nuclear Magnetic Resonance Spectrum (CDCl$_3$) δ ppm:
- 1.51 (3H, singlet);
- 1.74 (3H, singlet);
- 3.63–3.72 (2H, multiplet);
- 4.13 (1H, singlet);
- 4.59 (2H, triplet, J=5 Hz);
- 6.52 (1H, singlet);
- 6.95 (1H, broad singlet).

EXAMPLE 5

N-(2-Nitrooxyethyl)-5-(furan-2-yl)-2-oxothiazolidine-4-carboxamide (Compound No. 1-10)

1.58 ml of triethylamine and 0.47 ml of diethyl cyanophosphonate were added, whilst ice-cooling and stirring, to a suspension of 500 mg of 5-(furan-2-yl)-2-oxothiazolidine-4-carboxylic acid and 476 mg of N-(2-nitrooxyethyl)amine nitrate in 50 ml of dry tetrahydrofuran, and the resulting mixture was stirred at room temperature for 3.5 hours, after which the solvent was removed by distillation under reduced pressure. The crystals which precipitated were triturated with diisopropyl ether and collected by filtration. These crystals were recrystallized from methylene chloride, to give 400 mg of the title compound as colorless crystals, melting at 117°–118° C.

Nuclear Magnetic Resonance Spectrum (CDCl$_3$+hexadeuterated dimethyl sulfoxide) δ ppm:
- 3.53–3.74 (2H, multiplet);
- 4.41 (1H, singlet);
- 4.57 (2H, triplet, J=5 Hz);
- 5.37 (1H, doublet, J=3 Hz);
- 6.34–6.38 (2H, multiplet);
- 7.40 (1H, singlet);
- 7.80 (1H, singlet);
- 7.87 (1H, broad singlet).

EXAMPLE 6

N-Methyl-N-(2-nitrooxyethyl)-2-oxothiazolidine-4-carboxamide monohydrate (Compound No. 1-26)

0.95 ml of triethylamine, 1.0 g of 2-oxothiazolidine-4-carboxylic acid and 1.30 g of 1-(N,N-dimethylaminopropyl)-3-ethylcarbodiimide hydrochloride were added, whilst ice-cooling and stirring, to a suspension of 1.24 g of N-methyl-N-(2-nitrooxyethyl)amine nitrate in 50 ml of dry N,N-dimethylformamide, and the resulting mixture was stirred at room temperature for 45 minutes, after which the solvent was removed by distillation under reduced pressure. The residue was mixed with ethyl acetate, and the resulting mixture was washed with a saturated aqueous solution of sodium chloride and dried over anhydrous magnesium sulfate. The solvent was then removed by distillation under reduced pressure. The residual yellow oil was purified by column chromatography through silica gel, using a 4:1 by volume mixture of methylene chloride and ethyl acetate as the eluent. The colorless oil thus obtained was triturated with a small amount of tetrahydrofuran to induce crystallization. The crystals which precipitated were collected by filtration and recrystallized from acetone, to give 50 mg of the title compound as colorless crystals, melting at 110°–112° C.

Nuclear Magnetic Resonance Spectrum (hexadeuterated dimethyl sulfoxide) δ ppm:
- 2.64 (3H, singlet);
- 3.23–3.27 (2H, multiplet);
- 3.60 (1H, doublet of doublets, J=4 and 12 Hz);
- 3.77 (1H, doublet of doublets, J=8 and 12 Hz);
- 4.33–4.37 (2H, multiplet);
- 4.70 (1H, doublet of doublets, J=4 and 8 Hz);
- 8.47 (1H, singlet).

EXAMPLE 7

N-(2-Nitrooxyethyl)-3-methyl-2-oxothiazolidine-4-carboxamide (Compound No. 1-2)

1.33 ml of triethylamine and 0.36 ml of diethyl cyanophosphonate were added, whilst ice-cooling and stirring, to a suspension of 402 mg of N-(2-nitrooxyethyl)amine nitrate and 326 mg of 3-methyl-2-oxothiazolidine-4-carboxylic acid in 35 ml of dry tetrahydrofuran, and the resulting mixture was stirred at room temperature for 3.5 hours, after which the solvent was removed by distillation under reduced pressure. The residue was mixed with ethyl acetate, and the resulting mixture was washed with a saturated aqueous solution of sodium chloride. It was then dried over anhydrous magnesium sulfate, and the solvent was removed by distillation under reduced pressure. The crystalline residue was recrystallized from ethanol, to give 247 mg of the title compound as colorless crystals, melting at 105°–106° C.

Nuclear Magnetic Resonance Spectrum (CDCl$_3$) δ ppm:
- 2.94 (3H, singlet);
- 3.32 (1H, doublet of doublets, J=4 and 12 Hz);
- 3.63–3.78 (3H, multiplet);
- 4.23 (1H, doublet of doublets, J=4 and 9 Hz);
- 4.56–4.67 (2H, multiplet);
- 7.13 (1H, broad singlet).

EXAMPLE 8

N-(2-Nitrooxyethyl)-5-(1-naphthyl)-2-oxothiazolidine-4-carboxamide (Compound No. 1-25)

1.23 ml of triethylamine and 0.36 ml of diethyl cyanosphonate were added, whilst ice-cooling and stirring, to a suspension of 370 mg of N-(2-nitrooxyethyl)amine nitrate and 500 mg of 5-(1-naphthyl)-2-oxothiazolidine-4-carboxylic acid in 50 ml of dry tetrahydrofuran, and the resulting mixture was stirred at room temperature for 4 hours. At the end of this time, the solvent was removed by distillation under reduced pressure, and the residue was mixed with ethyl acetate. The resulting mixture was washed with a saturated aqueous solution of sodium chloride and then dried over anhydrous magnesium sulfate. The solvent was then removed by distillation under reduced pressure, and the crystalline residue was recrystallized from ethanol, to give 367 mg of the title compound as colorless crystals, melting at 151°–153° C.

Nuclear Magnetic Resonance Spectrum ($CDCl_3$ + hexadeuterated dimethyl sulfoxide) δ ppm:
3.40–3.60 (2H, multiplet);
4.51 (1H, doublet, J=3 Hz);
4.55 (2H, triplet, J=5 Hz);
5.83 (1H, doublet, J=3 Hz);
7.53–7.64 (3H, multiplet);
7.76 (1H, doublet, J=7 Hz);
7.91–8.03 (2H, multiplet);
8.18 (1H, doublet, J=7 Hz);
8.52 (1H, triplet, J=6 Hz);
8.61 (1H, singlet).

EXAMPLE 9

N-(2-Nitrooxyethyl)-2-oxo-5-(2-thienyl)thiazolidine-4-carboxamide (Compound No. 1-8)

A procedure similar to that described in Example 1 was repeated, but using 350 mg of N-(2-nitrooxyethyl)-amine nitrate and 400 mg of 2-oxo-5-(2-thienyl)thiazolidine-4-carboxylic acid, to obtain 260 mg of the title compound as colorless crystals, melting at 120°–122° C. (after recrystallization from ethanol).

Nuclear Magnetic Resonance Spectrum ($CDCl_3$ + hexadeuterated dimethyl sulfoxide) δ ppm:
3.50–3.78 (2H, multiplet);
4.28–4.30 (1H, multiplet);
4.57 (2H, triplet, J=5 Hz);
5.56 (1H, doublet, J=3 Hz);
6.95 (1H, doublet of doublets, J=3 and 5 Hz);
7.13 (1H, doublet, J=3 Hz);
7.26 (1H, doublet, J=5 Hz);
7.74 (1H, singlet);
7.77 (1H, broad singlet).

EXAMPLE 10

N-(2-Nitrooxyethyl)-2-oxo-5-(3-pyridyl)thiazolidine-4-carboxamide (Compound No. 1-16)

A procedure similar to that described in Example 1 was repeated, but using 300 mg of N-(2-nitrooxyethyl)-amine nitrate and 330 mg of 2-oxo-5-(3-pyridyl)thiazolidine-4-carboxylic acid, to obtain 140 mg of the title compound as colorless crystals, melting at 139°–140° C. (after recrystallization from ethanol).

Nuclear Magnetic Resonance Spectrum ($CDCl_3$ + hexadeuterated dimethyl sulfoxide) δ ppm:
3.50–3.75 (2H, multiplet);
4.21 (1H, doublet, J=3 Hz);
4.57 (2H, doublet of doublets, J=5 and 12 Hz);
5.31 (1H, doublet, J=3 Hz);
7.31 (1H, doublet of doublets, J=5 and 8 Hz);
7.78–7.92 (2H, multiplet);
8.57 (1H, doublet, J=5 Hz);
8.72 (1H, singlet).

EXAMPLE 11

N-(2-Nitrooxyethyl)-5-(3-nitrophenyl)-2-oxothiazolidine-4-carboxamide (Compound No. 1-12)

A procedure similar to that described in Example 1 was repeated, but using 380 mg of N-(2-nitrooxyethyl)-amine nitrate and 500 mg of 5-(3-nitrophenyl)-2-oxothiazolidine-4-carboxylic acid, to obtain 450 mg of the title compound as a pale yellow powder.

Nuclear Magnetic Resonance Spectrum ($CDCl_3$) δ ppm:
3.65–3.85 (2H, multiplet);
4.35 (1H, doublet, J=3 Hz);
4.64 (2H, triplet, J=3 Hz);
5.30 (1H, doublet, J=3 Hz);
7.02 (1H, singlet);
7.27 (1H, broad singlet);
7.62 (1H, triplet, J=8 Hz);
7.84 (1H, doublet, J=8 Hz);
8.22 (1H, doublet, J=8 Hz);
8.38 (1H, singlet).

EXAMPLE 12

N-(2-Nitrooxyethyl)-5-(4-methoxyphenyl)-2-oxothiazolidine-4-carboxamide (Compound No. 1-14)

A procedure similar to that described in Example 1 was repeated, but using 401 mg of N-(2-nitrooxyethyl)-amine nitrate and 500 mg of 5-(4-methoxyphenyl)-2-oxothiazolidine-4-carboxylic acid, to obtain 408 mg of the title compound as colorless crystals, melting at 142°–143° C. (after recrystallization from methylene chloride).

Nuclear Magnetic Resonance Spectrum ($CDCl_3$ + hexadeuterated dimethyl sulfoxide) δ ppm:
3.50–3.72 (2H, multiplet);
3.81 (3H, singlet);
4.20 (1H, doublet, J=3 Hz);
4.56 (2H, triplet, J=5 Hz);
5.21 (1H, doublet, J=3 Hz);
6.87 (2H, doublet, J=9 Hz);
7.40 (1H, doublet, J=9 Hz);
7.67 (1H, singlet);
7.76 (1H, broad singlet).

EXAMPLE 13

N-(2-Nitrooxyethyl)-5-(4-chlorophenyl)-2-oxothiazolidine-4-carboxamide (Compound No. 1-13)

A procedure similar to that described in Example 1 was repeated, but using 394 mg of N-(2-nitrooxyethyl)-amine nitrate and 500 mg of 5-(4-chlorophenyl)-2-oxothiazolidine-4-carboxylic acid, to obtain 350 mg of the title compound as colorless needles, melting at 125°–127° C. (after recrystallization from methylene chloride).

Nuclear Magnetic Resonance Spectrum ($CDCl_3$ + hexadeuterated dimethyl sulfoxide) δ ppm:
3.50–3.80 (2H, multiplet);
4.18 (1H, singlet);
4.57 (2H, triplet, J=5 Hz);

5.24 (1H, doublet, J=3 Hz);
7.33 (2H, doublet, J=9 Hz);
7.43 (1H, doublet, J=9 Hz);
7.91 (1H, singlet);
7.94 (1H, broad singlet).

EXAMPLE 14

N-(3-Nitrooxypropyl)-2-oxothiazolidine-4-carboxamide (Compound No. 1-68)

A procedure similar to that described in Example 1 was repeated, but using 1.25 g of N-(3-nitrooxypropyl)-amine nitrate and 1.0 g of 2-oxothiazolidine-4-carboxylic acid, to obtain 0.60 g of the title compound as pale yellow crystals, melting at 83°–85° C.

Nuclear Magnetic Resonance Spectrum (CDCl$_3$) δ ppm:
2.01 (2H, multiplet);
3.35–3.56 (2H, multiplet);
3.63 (1H, doublet of doublets, J=4 and 11 Hz);
3.81 (1H, doublet of doublets, J=4 and 11 Hz);
4.34–4.40 (1H, multiplet);
4.54 (2H, triplet, J=6 Hz);
6.97 (1H, singlet);
7.04 (1H, broad singlet).

EXAMPLE 15

N-(2-Nitrooxyethyl)-5-benzyl-2-oxothiazolidine-4-carboxamide (Compound No. 1-28)

A procedure similar to that described in Example 1 was repeated, but using 210 mg of N-(2-nitrooxyethyl)-amine nitrate and 250 mg of 5-benzyl-2-oxothiazolidine-4-carboxylic acid, to obtain 220 mg of the title compound as pale yellow columnar crystals, melting at 123°124° C. (after recrystallization from ethanol).

Nuclear Magnetic Resonance Spectrum (CDCl$_3$+hexadeuterated dimethyl sulfoxide) δ ppm:
3.09 (1H, doublet of doublets, J=9 and 14 Hz);
3.23 (1H, doublet of doublets, J=7 and 14 Hz);
3.45–3.75 (2H, multiplet);
4.03 (1H, singlet);
4.30–4.40 (1H, multiplet);
4.55 (2H, triplet, J=5 Hz);
7.20–7.38 (5H, multiplet);
7.53 (1H, singlet);
7.68 (1H, broad singlet).

EXAMPLE 16

(4R)-N-(2-Nitrooxyethyl)-2-oxothiazolidine-4-carboxamide (Compound No. 1-1)

16(a)
(4R)-N-(2-Hydroxyethyl)-2-oxothiazolidine-4-carboxamide 0.9 ml of oxalyl chloride and one drop of N,N-dimethylformamide were added to a suspension of 1.0 g of (4R)-2-oxothiazolidine-4-carboxylic acid in 20 ml of benzene, and the resulting mixture was stirred at room temperature for 1.5 hours. At the end of this time, the solvent was removed by distillation under reduced pressure. A solution of the residual pale yellow oil dissolved in 10 ml of methylene chloride was then added dropwise to a solution of 1.25 g of 2-ethanolamine in 25 ml of methylene chloride, whilst ice-cooling, and the mixture was stirred for 1.5 hours, whilst ice-cooling. The solvent was then removed by distillation under reduced pressure, and the resulting residue was purified by column chromatography through silica gel, using a 9:1 by volume mixture of methylene chloride and methanol as the eluent. The colorless crystals thus obtained were further recrystallized from ethyl acetate, to give 0.65 g of the title compound as colorless plates, melting at 116°–118° C.

Nuclear Magnetic Resonance Spectrum (CDCl$_3$+hexadeuterated dimethyl sulfoxide) δ ppm:
3.20–3.40 (1H, multiplet);
3.50–3.80 (5H, multiplet);
4.33 (1H, multiplet);
7.36 (1H, broad singlet);
7.57 (1H, singlet).

16(b)
(4R)-N-(2-Nitrooxyethyl)-2-oxothiazolidine-4-carboxamide 0.44 g of nitronium tetrafluoroborate and a solution of 0.41 g of 2,4,6-collidine in 20 ml of acetonitrile were added at a temperature of from −10° C. to 0° C. to 30 ml of acetonitrile, and the resulting mixture was stirred at the same temperature for 30 minutes. At the end of this time, 0.50 g of (4R)-N-(2-hydroxyethyl)-2-oxothiazolidine-4-carboxamide was added to the mixture, and the mixture was stirred at room temperature for 4 hours. The reaction mixture was then freed from the solvent by distillation under reduced pressure. The residue was mixed with ethyl acetate and insoluble materials were filtered off. The filtrate was concentrated by evaporation under reduced pressure, and the resulting residue was purified by column chromatography through silica gel, using ethyl acetate as the eluent. The pale yellow crystals thus obtained were recrystallized from ethyl acetate, to give 86 mg of the title compound as colorless crystals. The melting point and nuclear magnetic resonance spectrum of the product were identical with those of the compound produced as described in Example 1.

EXAMPLE 17

(4R)-N-[1-(Nitrooxymethyl)ethyl]-2-oxothiazolidine-4-carboxamide (Compound No. 1-30)

A procedure similar to that described in Example 1 was repeated, but using 1.5 g of (4R)-2-oxothiazolidine-4-carboxylic acid and 2.3 g of 1-(nitrooxymethyl)ethylamine nitrate, to obtain 0.35 g of the title compound as colorless crystals, melting at 112°–114° C. (after recrystallization from ethanol).

Nuclear Magnetic Resonance Spectrum (CDCl$_3$+hexadeuterated dimethyl sulfoxide) δ ppm:
1.27 (3H, doublet, J=7 Hz);
3.68 (2H, doublet, J=7 Hz);
4.25–4.60 (4H, multiplet);
7.49 (1H, doublet, J=7 Hz);
7.72 (1H, singlet).

EXAMPLE 18

(4R)-N-(2-Nitrooxypropyl)-2-oxothiazolidine-4-carboxamide (Compound No. 1-31)

A procedure similar to that described in Example 1 was repeated, but using 2.0 g of (4R)-2-oxothiazolidine-4-carboxylic acid and 3.0 g of N-(2-nitrooxypropyl)amine nitrate, to obtain 24 mg of the title compound as pale yellow crystals, melting at 70°–72° C. (after recrystallization from ethanol).

Nuclear Magnetic Resonance Spectrum (CDCl$_3$) δ ppm:
1.38 (3H, doublet, J=6 Hz);

3.35–3.90 (4H, multiplet);
4.35–4.50 (1H, multiplet);
5.20–5.40 (1H, multiplet);
6.99 (1H, singlet);
7.16 (1H, broad singlet).

EXAMPLE 19

(4S)-N-(2-Nitrooxyethyl)-2-oxooxazolidine-4-carboxamide (Compound No. 1-34)

3.2 ml of triethylamine and 1.5 ml of diethyl cyanophosphonate were added, whilst ice-cooling, to a suspension of 1.0 g of (4S)-2-oxooxazolidine-4-carboxylic acid and 1.55 g of N-(2-nitrooxyethyl)amine nitrate in 20 ml of dry tetrahydrofuran, and the resulting mixture was stirred at room temperature for 2 hours. At the end of this time, the solvent was removed by distillation under reduced pressure, and the residue was diluted with ethyl acetate; the mixture was then washed with a saturated aqueous solution of sodium chloride, after which it was dried over anhydrous magnesium sulfate. The solvent was then removed by distillation under reduced pressure, and the residual brown oil thus obtained was purified by column chromatography through silica gel, using ethyl acetate as the eluent, to give the title compound as yellowish brown crystals. These crude crystals were recrystallized from ethyl acetate, to give 0.25 g of the title compound as colorless needles, melting at 102°–103° C.

Nuclear Magnetic Resonance Spectrum ($CDCl_3$ + hexadeuterated dimethyl sulfoxide) δ ppm:
  3.40–3.58 (2H, multiplet);
  4.10–4.30 (2H, multiplet);
  4.45 (1H, triplet, J=8 Hz);
  4.56 (2H, triplet, J=5 Hz);
  7.96 (1H, singlet);
  8.42 (1H, triplet, J=5 Hz).

EXAMPLE 20

(4S,5R)-N-(2-Nitrooxyethyl)-5-methyl-2-oxooxazolidine-4-carboxamide (Compound No. 1-35)

A procedure similar to that described in Example 19 was repeated, but using 180 mg of (4S,5R)-5-methyl-2-oxooxazolidine-4-carboxylic acid and 230 mg of N-(2-nitrooxyethyl)amine nitrate, after which the product was recrystallized from methylene chloride, to obtain 41 mg of the title compound as colorless needles, melting at 81.5°–82.5° C.

Nuclear Magnetic Resonance Spectrum ($CDCl_3$ + hexadeuterated dimethyl sulfoxide) δ ppm:
  1.55 (3H, doublet, J=6 Hz);
  3.53–3.71 (2H, multiplet);
  3.89 (1H, doublet, J=7 Hz);
  4.58 (2H, triplet, J=5 Hz);
  4.65–4.75 (1H, multiplet);
  7.17 (1H, broad singlet);
  7.80 (1H, broad singlet).

EXAMPLE 21

(4S,5R)-N-(2-Nitrooxyethyl)-2-oxo-5-phenyloxazolidine-4-carboxamide (Compound No. 1-40)

A procedure similar to that described in Example 19 was repeated, but using 130 mg of (4S,5R)-2-oxo-5-phenyloxazolidine-4-carboxylic acid and 127 mg of N-(2-nitrooxyethyl)amine nitrate, to obtain 72 mg of the title compound as colorless plates, melting at 122°–124° C.

Nuclear Magnetic Resonance Spectrum ($CDCl_3$ + hexadeuterated dimethyl sulfoxide) δ ppm:
  3.58–3.69 (2H, multiplet);
  4.16 (1H, doublet, J=5 Hz);
  4.60 (2H, triplet, J=5 Hz);
  5.66 (1H, doublet, J=5 Hz);
  7.33–7.53 (6H, multiplet);
  7.99 (1H, broad singlet).

EXAMPLE 22

N-(2-Nitrooxyethyl)-2-oxo-5-(2-thienyl)oxazolidine-4-carboxamide (Compound No. 1-41)

A procedure similar to that described in Example 19 was repeated, but using 500 mg of 2-oxo-5-(2-thienyl)oxazolidine-4-carboxylic acid and 480 mg of N-(2-nitrooxyethyl)amine nitrate, to obtain 190 mg of the title compound as pale yellow plates, melting at 101°–103° C.

Nuclear Magnetic Resonance Spectrum ($CDCl_3$ + hexadeuterated dimethyl sulfoxide) δ ppm:
  3.54–3.73 (2H, multiplet);
  4.32 (1H, doublet, J=5 Hz);
  4.58 (2H, triplet, J=5 Hz);
  5.88 (1H, doublet, J=5 Hz);
  7.02 (1H, triplet, J=3 Hz);
  7.19 (1H, doublet, J=3 Hz);
  7.35 (1H, doublet, J=6 Hz);
  7.58 (1H, broad singlet);
  7.80 (1H, broad singlet).

EXAMPLE 23

N-(2-Nitrooxyethyl)-2-oxothiazolidine-5-carboxamide (Compound No. 2-1)

0.85 ml of triethylamine and 0.53 ml of diphenylphosphoryl azide were added, whilst ice-cooling, to a suspension of 0.30 g of 2-oxothiazolidine-5-carboxylic acid (prepared as described in Preparation 3) and 0.41 g of N-(2-nitrooxyethyl)amine nitrate in 10 ml of dry tetrahydrofuran, and the resulting mixture was stirred at room temperature for 2.5 hours. At the end of this time, the solvent was removed by distillation under reduced pressure, and the residue was purified by column chromatography through silica gel, using ethyl acetate as the eluent. The crude crystals thus obtained were triturated with diisopropyl ether, collected by filtration and washed to give 0.40 g of the title compound as a colorless powder, melting at 114°–115° C.

Nuclear Magnetic Resonance Spectrum ($CDCl_3$ + hexadeuterated dimethyl sulfoxide) δ ppm:
  3.50–3.67 (2H, multiplet);
  3.68–3.80 (1H, multiplet);
  3.90 4.02 (1H, multiplet);
  4.34 (1H, doublet of doublets, J=4 and 8 Hz);
  4.57 (2H, triplet, J=5 Hz);
  6.96 (1H, broad singlet);
  7.90 (1H, broad singlet).

EXAMPLE 24

(5S)-N-(2-Nitrooxyethyl)-2-oxooxazolidine-5-carboxamide (Compound No. 2-34)

0.35 ml of triethylamine and 0.22 ml of diphenylphosphoryl azide were added, whilst ice-cooling and stirring, to a suspension of 110 mg of (5S)-2-oxooxazolidine-5-carboxylic acid (prepared by a procedure similar to that described in Preparation 3) and 170 mg of N-(2-nitrooxyethyl)amine nitrate in 10 ml of dry tetrahydrofuran, and the resulting mixture was stirred at room temperature for 6 hours. At the end of this time, the solvent was removed by distillation under reduced pressure, and the residue was purified by column chromatography through silica gel, using ethyl acetate as the eluent. The pale yellow oil thus obtained was triturated with ethyl acetate, and the resulting precipitate was collected by filtration and washed, to give 79.8 mg of the title compound as a colorless powder, melting at 101°–103° C.

Nuclear Magnetic Resonance Spectrum ($CDCl_3$ + hexadeuterated dimethyl sulfoxide) δ ppm:
3.55–3.78 (3H, multiplet);
3.88 (1H, triplet, J=9 Hz);
4.58 (2H, triplet, J=5 Hz);
4.94 (1H, doublet of doublets, J=5 and 9 Hz);
6.72 (1H, singlet);
7.62 (1H, broad singlet).

EXAMPLE 25

(4R)-N-(4-Nitrooxybutyl)-2-oxothiazolidine-4-carboxamide (Compound No. 1-67)

25(a)
(4R)-N-(4-Hydroxybutyl)-2-oxothiazolidine-4-carboxamide

Following a procedure similar to that described in Example 16(a), but using 1.2 g of (4R)-2-oxothiazolidine-4-carboxylic acid and 2.23 g of N-(4-hydroxybutyl)amine, 0.735 g of the title compound was obtained as colorless crystals, melting at 81°–83° C.

Nuclear Magnetic Resonance Spectrum ($CDCl_3$ + hexadeuterated dimethyl sulfoxide) δ ppm:
1.51–1.75 (4H, multiplet);
3.25–3.40 (3H, multiplet);
3.55–3.75 (4H, multiplet);
4.27 (1H, triplet, J=7 Hz);
7.44 (1H, broad singlet);
7.76 (1H, singlet).

25(b)
(4R)-N-(4-Nitrooxybutyl)-2-oxothiazolidine-4-carboxamide

Following a procedure similar to that described in Example 16(b), but using 195 mg of nitronium tetrafluoroborate, 157 mg of 2,4,6-collidine and 218 mg of (4R)-N-(4-hydroxybutyl)-2-oxothiazolidine-4-carboxamide [prepared as described in step (a) above], 55 mg of the title compound were obtained as colorless needles, melting at 68°–70° C.

Nuclear Magnetic Resonance Spectrum ($CDCl_3$) δ ppm:
1.60–1.87 (4H, multiplet);
3.25 3.46 (2H, multiplet);
3.61 (1H, doublet of doublets, J=5 and 11 Hz);
3.79 (1H, doublet of doublets, J=9 and 11 Hz);
4.38 (1H, doublet of doublets, J=5 and 9 Hz);
4.49 (2H, triplet, J=6 Hz);
7.15 (1H, triplet, J=6 Hz);
7.35 (1H, singlet).

EXAMPLE 26

(4S)-N-(2-Nitrooxyethyl)-2-oxothiazolidine-4-carboxamide (Compound No. 1-1)

Following a procedure similar to that described in Example 1, but using 1.0 g of (4S)-2-oxothiazolidine-4-carboxylic acid and 1.15 g of N-(2-nitrooxyethyl)amine nitrate, 0.50 g of the title compound was obtained as pale yellow needles, melting at 129°–130° C. (with decomposition).

Nuclear Magnetic Resonance Spectrum (hexadeuterated dimethyl sulfoxide) δ ppm:
3.30–3.37 (1H, multiplet);
3.47 (2H, doublet of doublets, J=5 and 11 Hz);
3.63–3.71 (1H, multiplet);
4.25–4.30 (1H, multiplet);
4.56 (2H, triplet, J=5 Hz);
8.28 (1H, singlet);
8.36 (1H, triplet, J=5 Hz).

EXAMPLE 27

(4R)-N-(2-Nitrooxyethyl)-2-oxooxazolidine-4-carboxamide (Compound No. 1-34)

Following a procedure similar to that described in Example 1, but using 0.23 g of (4R)-2-oxooxazolidine-4-carboxylic acid and 0.36 g of N-(2-nitrooxyethyl)amine nitrate, 0.16 g of the title compound was obtained as colorless needles, melting at 110°–112° C.

Nuclear Magnetic Resonance Spectrum ($CDCl_3$ and hexadeuterated dimethyl sulfoxide) δ ppm:
3.47–3.72 (2H, multiplet);
4.30–4.36 (1H, multiplet);
4.47 4.63 (4H, multiplet);
7.31 (1H, singlet);
7.89 (1H, broad singlet).

EXAMPLE 28

(5R)-N-(2-Nitrooxyethyl)-2-oxooxazolidine-5-carboxamide (Compound No. 2-34)

Following a procedure similar to that described in Example 1, but using 0.32 g of (5R)-2-oxooxazolidine-5-carboxylic acid, 0.50 g of N-(2-nitrooxyethyl)amine nitrate and 0.63 ml of diphenylphosphoryl azide, 0.11 g of the title compound was obtained as pale yellow plates, melting at 103°–105° C.

Nuclear Magnetic Resonance Spectrum ($CDCl_3$ and hexadeuterated dimethyl sulfoxide) δ ppm:
3.57–3.77 (3H, multiplet);
3.90 (1H, triplet, J=9 Hz);
4.60 (2H, triplet, J=5 Hz);
4.96 (1H, doublet of doublets, J=5 and 9 Hz);
6.64 (1H, singlet);
7.58 (1H, broad singlet).

EXAMPLE 29

(4R,5S)-N-(2-Nitrooxyethyl)-4-methyl-2-oxooxazolidine-5-carboxamide (Compound No. 2-38)

Following a procedure similar to that described in Example 1, but using 167 mg of (4R,5S)-2-oxo-4-methyloxazolidine-5-carboxylic acid, 234 mg of N-(2-nitrooxyethyl)amine nitrate and 0.30 ml of diphenylphosphoryl azide, 40 mg of the title compound were obtained as a colorless oil.

Nuclear Magnetic Resonance Spectrum ($CDCl_3$ and hexadeuterated dimethyl sulfoxide) δ ppm:
1.44 (3H, doublet, J=6 Hz);
3.57–3.72 (2H, multiplet);
3.94–4.04 (1H, multiplet);
4.43 (1H, doublet, J=6 Hz);
4.58 (2H, triplet, J=5 Hz);
6.86 (1H, singlet);
7.59 (1H, broad singlet).

EXAMPLE 30

(4S,5R)-N-(2-Nitrooxyethyl)-4-methyl-2-oxooxazolidine-5-carboxamide (Compound No. 2-38)

Following a procedure similar to that described in Example 1, but using 312 mg of (4S,5R)-2-oxo-4-methyloxazolidine-5-carboxylic acid, 372 mg of N-(2-nitrooxyethyl)amine nitrate and 0.47 ml of diphenylphosphoryl azide, 83 mg of the title compound were obtained as a colorless oil.

Nuclear Magnetic Resonance Spectrum (CDCl$_3$) δ ppm:
 1.46 (3H, doublet, J=7 Hz);
 3.57–3.75 (2H, multiplet);
 4.00–4.10 (1H, multiplet);
 4.49 (1H, doublet, J=6 Hz);
 4.52–4.66 (2H, multiplet);
 6.23 (1H, singlet);
 7.44 (1H, triplet, J=6 Hz).

EXAMPLE 31

N-(2-Nitrooxyethyl)-4-phenyl-2-oxooxazolidin-5-carboxamide (Compound No. 2-40)

Following a procedure similar to that described in Example 1, but using 112 mg of 2-oxo-4-phenyloxazolidine-5-carboxylic acid, 110 mg of N-(2-nitrooxyethyl)amine nitrate and 0.24 ml of diphenylphosphoryl azide, 12 mg of the title compound were obtained as colorless crystals, melting at 122°–124° C.

Nuclear Magnetic Resonance Spectrum (CDCl$_3$ and hexadeuterated dimethyl sulfoxide) δ ppm:
 3.62–3.76 (2H, multiplet);
 4.55–4.65 (2H, multiplet);
 4.70 (1H, doublet, J=5 Hz);
 5.05 (1H, doublet, J=5 Hz);
 6.45 (1H, singlet);
 7.30–7.43 (6H, multiplet).

PREPARATION 1

Methyl 3-(N-benzyldithiocarbonylamino)-2-hydroxypropionate 5 ml of a 4 N solution of hydrogen chloride in dioxane were added to a suspension of 2.0 g of DL-isoserine in 20 ml of methanol, and the resulting mixture was allowed to stand at room temperature for 2 days and nights. At the end of this time, the solvent was removed by distillation under reduced pressure, the resulting residue was mixed with benzene and the solvent was removed by azeotropic distillation to dryness. The residue was dissolved in 13 ml of pyridine, and 2.8 ml of triethylamine and 1.6 ml of carbon disulfide were added, whilst ice-cooling and stirring, to the solution. The resulting mixture was then stirred at room temperature for 4 hours, after which 1.6 ml of benzyl chloride was added, and the reaction mixture was then allowed to stand overnight, whilst ice-cooling. At the end of this time, it was poured into ice-water and extracted with diethyl ether. The extract was then washed first with 1 N aqueous hydrochloric acid and then with an aqueous solution of sodium hydrogencarbonate, after which it was dried over anhydrous magnesium sulfate. After the solvent had been removed by distillation under reduced pressure, the residue was purified by column chromatography through silica gel, using a 1:2 by volume mixture of ethyl acetate and hexane as the eluent, to give 2.68 g of the title compound as a pale yellow oil.

Nuclear Magnetic Resonance Spectrum (CDCl$_3$) δ ppm:
 2.90–3.30 (1H, broad singlet);
 3.82 (3H, singlet);
 3.95–4.05 (1H, multiplet);
 4.13–4.32 (1H, multiplet);
 4.45 (1H, broad singlet);
 4.53 (2H, singlet);
 7.20–7.43 (6H, multiplet).

PREPARATION 2

3-Amino-2-(benzylthiocarbonylthio)propionic acid hydrochloride 2.0 ml of thionyl chloride were added, whilst ice-cooling, to 2.68 g of methyl 3-(N-benzyldithiocarbonylamino)-2-hydroxypropionate (prepared as described in Preparation 1), and the resulting mixture was stirred at the same temperature for 30 minutes. At the end of this time, it was freed from an excess of thionyl chloride by distillation under reduced pressure. The residual yellow oil thus obtained was mixed with 40 ml of 3 N aqueous hydrochloric acid, and the mixture was heated under reflux for 2 hours. The mixture was then cooled, after which the solvent was removed by distillation under reduced pressure. The residue was triturated with acetone, and the precipitated pale yellow crystals were collected by filtration, to give 1.42 g of the title compound, melting at 182°–185° C. (with decomposition).

Nuclear Magnetic Resonance Spectrum (CDCl$_3$+hexadeuterated dimethyl sulfoxide) δ ppm:
 3.10–3.60 (2H, multiplet);
 4.38 (2H, singlet);
 4.53 (1H, triplet, J=7 Hz);
 7.28–7.42 (5H, multiplet).

PREPARATION 3

2-Oxothiazolidine-5-carboxylic acid 12.0 ml of a 1 N aqueous solution of sodium hydroxide were added to a suspension of 1.2 g of 3-amino-2-(benzylthiocarbonylthio)propionic acid hydrochloride in 35 ml of ethanol, and the resulting mixture was stirred at room temperature for 30 minutes, after which 12.0 ml of 1 N aqueous hydrochloric acid were added, whilst ice-cooling. The solvent was then removed by distillation under reduced pressure, the resulting residue was dissolved in diethyl ether and the solution was dried over anhydrous magnesium sulfate. The solvent was then removed by distillation under reduced pressure, to give 0.50 g of a colorless powder. This powder was recrystallized from ethyl acetate, to give 0.25 g of the title compound as colorless columnar crystals, melting at 148°–150° C.

Nuclear Magnetic Resonance Spectrum (CDCl$_3$+hexadeuterated dimethyl sulfoxide) δ ppm:
 3.68–3.80 (1H, multiplet);
 3.94 (1H, doublet of doublets, J=5 and 10 Hz);
 4.43 (1H, doublet of doublets, J=5 and 8 Hz);
 6.34 (1H, broad singlet).

BIOLOGICAL ACTIVITY

The compounds of the present invention were found to have a potent collateral vessel dilating activity, and do not undergo the first pass effect, as demonstrated by the following experiment in anesthetized dogs, thus demonstrating that the compounds are very useful for the treatment and prevention of angina pectoris.

EXPERIMENT 1

Test Procedure for Collateral Vessel Dilating Effect

Male Beagle dogs, each weighing from 9 to 13 kg, were anesthetized by the intravenous injection of 30 mg/kg of pentobarbital, and then the systemic blood pressure was measured from the left femoral artery. In order to measure the peripheral blood pressure below the occulsion site of the carotid artery, a polyethylene cannula (Atom Venous Catheter, 2F) was inserted into one of the branch vessels of the left thyroidal artery. The left carotid artery was occluded by means of an artery clamp for one minute, and the blood pressure just before occulusion (P) and the maximum decrease of the peripheral blood pressure ($\Delta P$) were measured. Thereafter, a test sample was administered through a polyethylene cannula inserted into the femoral vein. 5, 15, 30, 45 and 60 minutes after administration of the test sample, the left carotid artery was occuluded, each time for one minute, and the blood pressure just before occulusion (P') and the maximum decrease of the peripheral blood pressure ($\Delta P'$) were again measured. The collateral vessel dilating effect of each test sample (the "collateral index", CI) was calculated by the following equation.

$$CI = 100 - (\Delta P'/P') \times 100/(\Delta P/P)$$

The compounds of Examples 1, 19 and 23 were all tested and all showed an excellent collateral vessel dilating effect in this test.

EXPERIMENT 2

Collateral Vessel Dilating Effect after Intraportal Administration

The test animals used were the same as in Experiment 1, and were prepared the same as in Experiment 1. In order to administer a test sample by the intra-portal route, the abdominal portion was incised along the median line, and one of the branch vessels of the mesenteric vein was exposed. A polyethylene cannula (Atom Venous Catheter, 2F) was inserted into the vein in the direction of the blood stream. To examine the first pass effect, a test sample was first administered intravenously and its collateral vessel dilating effect over 60 minutes was evaluated. After 2 to 3 hours, an identical sample was administered intraportally and its collateral vessel dilating effect over 60 minutes was evaluated.

The compounds of Examples 1, 19 and 23 were all tested and all showed an excellent collateral vessel dilating effect in this test.

We claim:

1. A compound of formula (I):

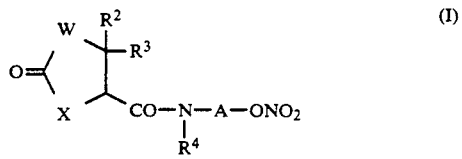

wherein:
W represents a sulfur atom and X represents a group of formula —N(R$^1$)—, or W represents a group of formula —N(R$^1$)— and X represents a sulfur atom;

R$^1$ represents a hydrogen atom, an alkyl group having from 1 to 6 carbon atoms or an aralkyl group in which an aryl group, as defined below, is a substituent on an alkyl group having from 1 to 4 carbon atoms;

R$^2$ and R$^3$ are independently selected from the group consisting of:
hydrogen atoms;
alkyl groups having from 1 to 6 carbon atoms;
aralkyl groups in which an aryl group, as defined below, is a substituent on an alkyl group having from 1 to 4 carbon atoms;
aryl groups, as defined below;
aromatic heterocyclic groups having an aromatic ring containing 5 or 6 ring atoms of which from 1 to 3 are hetero-atoms selected from the group consisting of nitrogen, oxygen and sulfur atoms and the remaining ring atoms are carbon, said heterocyclic group being unsubstituted or being substituted by at least one substituent selected from the group consisting of substituents (a), defined below; and
fused ring systems in which an aromatic heterocyclic group, as defined above, is fused to a benzene ring;

R$^4$ represents a hydrogen atom, an alkyl group having from 1 to 6 carbon atoms or an aralkyl group in which an aryl group, as defined below, is a substituent on an alkyl group having from 1 to 4 carbon atoms; and A represents an alkylene group having from 2 to 6 carbon atoms in a straight or branched carbon chain and being unsubstituted or being substituted by one carboxy substituent;

said aryl groups have from 6 to 10 ring carbon atoms in at least one aromatic ring and are unsubstituted or are substituted by at least one substituent selected from the group consisting of substituents (b), defined below;

substituents (a) are selected from the group consisting of:
alkyl groups having from 1 to 6 carbon atoms; and
groups of formula —NR$^a$R$^b$, where R$^a$ and R$^b$ are independently selected from the group consisting of hydrogen atoms and alkyl groups having from 1 to 6 carbon atoms;

substituents (b) are selected from the group consisting of
alkyl groups having from 1 to 6 carbon atoms;
alkoxy groups having from 1 to 6 carbon atoms;
halogen atoms;
groups of formula —NR$^a$R$^b$, where R$^a$ and R$^b$ are defined above;
hydroxy groups; and
nitro groups;

and pharmaceutically acceptable salts and esters thereof.

2. The compound of claim 1, wherein the compound is in the form of an ester and A represents said alkylene group which is substituted by at least one substituent selected from the group consisting of alkoxycarbonyl groups in which the alkoxy part has from 1 to 6 carbon atoms and aryloxcarbonyl groups in which the aryl part is as defined in claim 1.

3. The compound of claim 1, which has the formula (Ia):

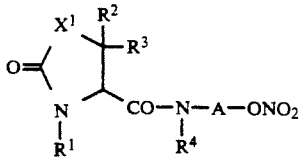

(Ia)

wherein A, $R^1$, $R^2$, $R^3$ and $R^4$ are defined in claim 1, and $X^1$ represents a sulfur atom.

4. The compound of claim 1, which has the formula (Ib):

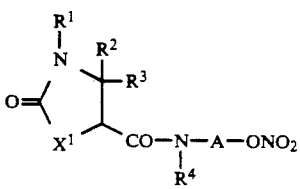

(Ib)

wherein A, $R^1$, $R^2$, $R^3$ and $R^4$ are as defined in claim 1, and $X^1$ represents a sulfur atom.

5. The compound of claim 1, wherein $R^1$ represents a hydrogen atom, an alkyl group having from 1 to 4 carbon atoms, a benzyl group or a phenethyl group.

6. The compound of claim 1, wherein $R^2$ and $R^3$ are independently selected from the group consisting of:
   hydrogen atoms;
   alkyl groups having from 1 to 4 carbon atoms;
   phenylalkyl groups in which the alkyl part has from 1 to 4 carbon atoms and the phenyl part is unsubstituted or is substituted by at least one substituent selected from the group consisting of alkyl groups having from 1 to 4 carbon atoms, alkoxy groups having from 1 to 4 carbon atoms, hydroxy groups, halogen atoms and nitro groups;
   naphthylmethyl groups;
   phenyl groups which are unsubstituted or are substituted by at least one substituent selected from the group consisting of alkyl groups having from 1 to 4 carbon atoms, alkoxy groups having from 1 to 4 carbon atoms, hydroxy groups, halogen atoms and nitro groups;
   naphthyl groups; and
   pyridyl, furyl, thienyl, oxazolyl, thiazolyl, isooxazolyl and isothiazolyl groups which are unsubstituted or are substituted by at least one substituent selected from the group consisting of alkyl groups having from 1 to 4 carbon atoms.

7. The compound of claim 1, wherein $R^4$ represents a hydrogen atom, an alkyl group having from 1 to 4 carbon atoms, a benzyl group or a phenethyl group.

8. The compound of claim 1, wherein A represents an alkylene group which has from 2 to 4 carbon atoms and which is unsubstituted or is substituted by one carboxy group.

9. The compound of claim 1, wherein:
   $R^1$ represents a hydrogen atom, an alkyl group having from 1 to 4 carbon atoms, a benzyl group or a phenethyl group;
   $R^2$ and $R^3$ are independently selected from the group consisting of:
   hydrogen atoms;
   alkyl groups having from 1 to 4 carbon atoms;
   phenylalkyl groups in which the alkyl part has from 1 to 4 carbon atoms and the phenyl part is unsubstituted or is substituted by at least one substituent selected from the group consisting of alkyl groups having from 1 to 4 carbon atoms, alkoxy groups having from 1 to 4 carbon atoms, hydroxy groups, halogen atoms and nitro groups;
   naphthylmethyl groups;
   phenyl groups which are unsubstituted or are substituted by at least one substituent selected from the group consisting of alkyl groups having from 1 to 4 carbon atoms, alkoxy groups having from 1 to 4 carbon atoms, hydroxy groups, halogen atoms and nitro groups;
   naphthyl groups; and
   pyridyl, furyl, thienyl, oxazolyl, thiazolyl, isooxazolyl and isothiazolyl groups which are unsubstituted or are substituted by at least one substituent selected from the group consisting of alkyl groups having from 1 to 4 carbon atoms;
   $R^4$ represents a hydrogen atom, an alkyl group having from 1 to 4 carbon atoms, a benzyl group or a phenethyl group; and
   A represents an alkylene group which has from 2 too 4 carbon atoms and which is unsubstituted or is substituted by one carboxy group.

10. The compound of claim 1, wherein:
    $R^1$ represents a hydrogen atom, a methyl group or a benzyl group;
    $R^2$ and $R^3$ are independently selected from the group consisting of:
    hydrogen atoms;
    methyl groups;
    benzyl and phenethyl groups which are unsubstituted or are substituted by at least one substituent selected from the group consisting of methyl groups, methoxy groups, fluorine atoms, chlorine atoms and hydroxy groups;
    phenyl groups which are unsubstituted or are substituted by at least one substituent selected from the group consisting of methyl groups, methoxy groups, fluorine atoms, chlorine atoms and hydroxy groups; and
    pyridyl, furyl and thienyl groups;
    $R^4$ represents a hydrogen atom, a methyl group or a benzyl group; and
    A represents an alkylene group which has from 2 to 4 carbon atoms.

11. The compound of claim 1, wherein:
    W represents a sulfur atom and X represents a group of formula —NH— or X represents a sulfur atom and W represents a group of formula —NH—;
    $R^2$ represents
    a hydrogen atom;
    a benzyl group which is unsubstituted or is substituted by at least one substituent selected from the group consisting of methyl groups, methoxy groups and hydroxy groups; or
    a phenyl group which is unsubstituted or is substituted by at least one substituent selected from the group consisting of methyl groups, methoxy groups and hydroxy groups;
    $R^3$ represents a hydrogen atom;
    $R^4$ represents a hydrogen atom; and
    A represents an alkylene group which has from 2 to 4 carbon atoms.

12. The compound of claim 1, wherein:
    W represents a sulfur atom and X represents a group of formula —NH—;

R² represents
  a hydrogen atom;
  a benzyl group;
  a phenyl group which is unsubstituted or is substituted by at least one substituent selected from the group consisting of methyl groups and methoxy groups;
R³ represents a hydrogen atom;
R⁴ represents a hydrogen atom; and
A represents an ethylene group.

13. The compound of claim 1, which is N-(2-nitrooxyethyl)-2-oxothiazolidine-4-carboxamide.

14. The compound of claim 1, which is N-(2-nitroxyethyl)-5-(4-methoxyphenyl)-2-oxothiazolidine-4-carboxamide.

15. The compound of claim 1, which is N-(2-nitrooxyethyl)-5-benzyl-2-oxothiazolidine-4-carboxamide.

16. The compound of claim 1, which is N-(2-nitrooxyethyl)-2-oxothiazolidine-5-carboxamide.

17. The compound of claim 1, which is N-(2-nitrooxyethyl)-4-(4-methoxyphenyl)-2-oxothiazolidine-5-carboxamide.

18. A composition for the treatment and prophylaxis of cardiovascular disorders or insufficiency, said composition comprising an effective amount of at least one coronary vasodilator in admixture with a pharmaceutically acceptable carrier or diluent, wherein said coronary vasodilator is selected from the group consisting of compounds of formula (I) and pharmaceutically acceptable salts and esters thereof, as claimed in claim 1.

19. The composition of claim 18, wherein:
R¹ represents a hydrogen atom, an alkyl group having from 1 to 4 carbon atoms, a benzyl group or a phenethyl group;
R² and R³ are independently selected from the group consisting of:
  hydrogen atoms;
  alkyl groups having from 1 to 4 carbon atoms;
  phenylalkyl groups in which the alkyl part has from 1 to 4 carbon atoms and the phenyl part is unsubstituted or is substituted by at least one substituent selected from the group consisting of alkyl groups having from 1 to 4 carbon atoms, alkoxy groups having from 1 to 4 carbon atoms, hydroxy groups, halogen atoms and nitro groups;
  naphthylmethyl groups
  phenyl groups which are unsubstituted or are substituted by at least one substituent selected from the group consisting of alkyl groups having from 1 to 4 carbon atoms, alkoxy groups having from 1 t 4 carbon atoms, hydroxy groups, halogen atoms and nitro groups;
  naphthyl groups; and
  pyridyl, furyl, thienyl, oxazolyl, thiazolyl, isooxazolyl and isothiazolyl groups which are unsubstituted or are substituted by at least one substituent selected from the group consisting of alkyl groups having from 1 to 4 carbon atoms;
R⁴ represents a hydrogen atom, an alkyl group having from 1 to 4 carbon atoms, a benzyl group or a phenethyl group; and
A represents an alkylene group which has from 2 to 4 carbon atoms and which is unsubstituted or is substituted by one carboxy group.

20. The composition of claim 18, wherein:
W represents a sulfur atom and X represents a group of formula —NH—;
R² represents
  a hydrogen atom;
  a benzyl group;
  a phenyl group which is unsubstituted or is substituted by at least one substituent selected from the group consisting of methyl groups and methoxy groups;
R³ represents a hydrogen atom;
R⁴ represents a hydrogen atom; and
A represents an ethylene group.

21. The composition of claim 18, wherein said coronary vasodilator is selected from the group consisting of:
  N-(2-nitrooxyethyl)-2-oxothiazolidine-4-carboxamide;
  N-(2-nitrooxyethyl)-5-(4-methoxyphenyl)-2-oxothiazolidine-4-carboxamide;
  N-(2-nitrooxyethyl)-5-benzyl-2-oxothiazolidine-4-carboxamide;
  N-(2-nitrooxyethyl)-2-oxothiazolidine-5-carboxamide; and
  N-(2-nitroooxyethyl)-4-(4-methoxyphenyl)-2-oxothiazolidine-5-carboxamide.

22. A method for the treatment or prophylaxis of cardiovascular disorders or insufficiency, which comprises administering at least one coronary vasodilator to a mammal suffering from or susceptible to cardiovascular disorders or insufficiency, wherein said cornary vasodialtor is selected from the group consisting of compounds of formula (I) and pharmaceutically acceptable salts and esters thereof, as claimed in claimed 1.

23. The method of claim 22, wherein:
R¹ represents a hydrogen atom, an alkyl group having from 1 to 4 carbon atoms, a benzyl group or a phenethyl group;
R² and R³ are independently selected from the group consisting of:
  hydrogen atoms;
  alkyl groups having from 1 to 4 carbon atoms;
  phenylalkyl groups in which the alkyl part has from 1 to 4 carbon atoms and the phenyl part is unsubstituted or is substituted by at least one substituent selected from the group consisting of alkyl groups having from 1 to 4 carbon atoms, alkoxy groups having from 1 to 4 carbon atoms, hydroxy groups, halogen atoms and nitro groups;
  naphthylmethyl groups;
  phenyl groups which are unsubstituted or are substituted by at least one substituent selected from the group consisting of alkyl groups having from 1 to 4 carbon atoms, alkoxy groups having from 1 to 4 carbon atoms, hydroxy groups, halogen atoms and nitro groups;
  naphthyl groups; and
  pyridyl, furyl, thienyl, oxazolyl, thiazolyl, isooxazolyl and isothiazolyl groups which are unsubstituted or are substituted by at least one substituent selected from the group consisting of alkyl groups having from 1 to 4 carbon atoms;
R⁴ represents a hydrogen atom, an alkyl group having from 1 to 4 carbon atoms, a benzyl group or a phenethyl group; and
A represents an alkylene group which has 2 to 4 carbon atoms and which is unsubstituted or is substituted by one carboxy group.

24. The method of claim 22, wherein:

W represents a sulfur atom and X represents a group of formula —NH—;

R² represents
a hydrogen atom;
a benzyl group;
a phenyl group which is unsubstituted or is substituted by at least one substituent selected from the group consisting of methyl groups and methoxy groups;

R³ represents a hydrogen atom;

R⁴ represents a hydrogen atom; and

A represents an ethylene group.

25. The method of claim 22, wherein said coronary vasodilator is selected from the group consisting of:
N-(2-nitrooxyethyl)-2-oxothiazolidine-4-carboxamide;
N-(2-nitrooxyethyl)-5-(4-methoxyphenyl)-2-oxothiazoolidine-4-carboxamide;
N-(2-nitrooxyethyl)-5-benzyl-2-oxothiazolidine-4-carboxamide;
N-(2-nitrooxyethyl)-2-oxothiazolidine-5-carboxamide; and
N-(2-nitrooxyethyl)-4-(4-methoxyphenyl)-2-oxothiazolidine-5-carboxamide.

26. The compound of claim 1, wherein the compound is in the form of an ester and wherein A represents said alkylene group which has to 2 to 4 carbon atoms, and which is substituted by an alkoxycarbonyl group in which the alkoxy part has from 1 to 4 carbon atoms.

27. The compound of claim 1, wherein the compound is in the form of an ester and
R¹ represents a hydrogen atom, an alkyl group having from 1 to 4 carbon atoms, a benzyl group or a phenethyl group;
R² and R³ are independently selected from the group consisting of:
hydrogen atoms;
alkyl groups having from 1 to 4 carbon atoms;
phenylalkyl groups in which the alkyl part has from 1 to 4 carbon atoms and the phenyl part is unsubstituted or is substituted by at least one substituent selected from the group consisting of alkyl groups having from 1 to 4 carbon atoms, alkoxy groups having from 1 to 4 carbon atoms, hydroxy groups, halogen atoms and nitro groups;
naphthylmethyl groups;
phenyl groups which are unsubstituted or are substituted by at least one substituent selected from the group consisting of alkyl groups having from 1 to 4 carbon atoms,alkoxy groups having from 1 to 4 carbon atoms, hydroxy groups, halogen atoms and nitro groups;
naphthyl groups; and
pyridyl, furyl, thienyl, oxazolyl, thiazolyl, isooxazolyl and isothiazolyl groups which are unsubstituted or are substituted by at least one substituent selected from the group consisting of alkyl groups having from 1 to 4 carbon atoms;
R⁴ represents a hydrogen atom, an alkyl group having from 1 to 4 carbon atoms, a benzyl group or a phenethyl group; and
A represents an alkylene group which has from 2 to 4 carbon atoms and which is substituted by an alkoxycarbonyl group in which the alkoxy part has from 1 to 4 carbon atoms.

28. The composition of claim 18, wherein the compound is in the form of an ester and
R¹ represents a hydrogen atom, an alkyl group having from 1 to 4 carbon atoms, a benzyl group or a phenethyl group;
R² and R³ are independently selected from the group consisting of;
hydrogen atoms;
alkyl groups having from 1 to 4 carbon atoms;
phenylalkyl groups in which the alkyl part has from 1 to 4 carbon atoms and the phenyl part is unsubstituted or is substituted by at least one substituent selected from the group consisting of alkyl groups having from 1 to 4 carbon atoms, alkoxy groups having from 1 to 4 carbon atoms, hydroxy groups, halogen atoms and nitro groups;
naphthylmethyl groups;
phenyl groups which are unsubstituted or are substituted by at least one substituent selected from the group consisting of alkyl groups having from 1 to 4 carbon atoms, alkoxy groups having from 1 to 4 carbon atoms, hydroxy groups, halogen atoms and nitro groups;
naphthyl groups; and
pyridyl, furyl, thienyl, oxazolyl, thiazolyl, isooxazolyl and isothiazolyl groups which are unsubstituted or are substituted by at least one substituent selected from the group consisting of alkyl groups having from 1 to 4 carbon atoms;
R⁴ represents a hydrogen atom, an alkyl group having from 1 to 4 carbon atoms, a benzyl group or a phenethyl group; and
A represents an alkylene group which has from 2 to 4 carbon atoms and which is substituted by at least one alkoxycarbonyl group in which the alkoxy part has from 1 to 4 carbon atoms.

29. The method of claim 22, wherein the compound is in the form of an ester and
R¹ represents a hydrogen atom, an alkyl group having from 1 to 4 carbon atoms, a benzyl group or a phenethyl group;
R² and R³ are independently selected from the group consisting of:
hydrogen atoms;
alkyl groups having from 1 to 4 carbon atoms;
phenylalkyl groups in which the alkyl part has from 1 t 4 carbon atoms and the phenyl part is unsubstituted or is substituted by at least one substituent selected from the group consisting of alkyl groups having from 1 to 4 carbon atoms, alkoxy groups having from 1 to 4 carbon atoms, hydroxy groups, halogen atoms and nitro groups;
naphthylmethyl groups;
phenyl groups which are unsubstituted or are substituted by at least one substituent selected from the group consisting of alkyl groups having from 1 to 4 carbon atoms, alkoxy groups having from 1 to 4 carbon atoms, hydroxy groups, halogen atoms and nitro groups;
naphthyl groups; and
pyridyl, furyl, thienyl, oxazolyl, thiazolyl, isooxazolyl and isothiazolyl groups which are unsubstituted or are substituted by at least one substituent selected from the group consisting of alkyl groups having from 1 to 4 carbon atoms;
R⁴ represents a hydrogen atom, an alkyl group having from 1 to 4 carbon atoms, a benzyl group or a phenethyl group; and
A represents an alkylene group which has from 2 to 4 carbon atoms and which is substituted by an alkoxycarbonyl group in which the alkoxy part has from 1 to 4 carbon atoms.

* * * * *